US008071839B2

(12) United States Patent
Mackay

(10) Patent No.: US 8,071,839 B2
(45) Date of Patent: Dec. 6, 2011

(54) TRANSGENIC MOUSE COMPRISING A POLYNUCLEOTIDE ENCODING HUMAN OR HUMANIZED C5AR AND METHODS OF PRODUCTION AND USE

(75) Inventor: Charles Reay Mackay, Vaucluse (AU)

(73) Assignee: G2 Inflammation Pty Ltd, Darlinghurst (AU)

( * ) Notice: Subject to any disclaimer, the term of this patent is extended or adjusted under 35 U.S.C. 154(b) by 0 days.

(21) Appl. No.: 10/584,480

(22) PCT Filed: Dec. 24, 2004

(86) PCT No.: PCT/AU2004/001844
§ 371 (c)(1),
(2), (4) Date: Apr. 17, 2007

(87) PCT Pub. No.: WO2005/060739
PCT Pub. Date: Jul. 7, 2005

(65) Prior Publication Data
US 2007/0277252 A1 Nov. 29, 2007

(30) Foreign Application Priority Data
Dec. 24, 2003 (AU) ................................ 2003907150

(51) Int. Cl.
*C12N 15/00* (2006.01)
(52) U.S. Cl. ................. 800/18; 800/3; 800/21; 435/325
(58) Field of Classification Search ................ 800/8, 18, 800/21, 3; 435/325
See application file for complete search history.

(56) References Cited

FOREIGN PATENT DOCUMENTS

| WO | WO9833908 | | 8/1994 |
|---|---|---|---|
| WO | WO 94/20142 | | 9/1994 |
| WO | WO 95/00164 | * | 1/1995 |
| WO | WO 98/24893 | | 6/1998 |
| WO | WO9833908 | | 8/1998 |
| WO | WO 02/061087 A2 | * | 8/2002 |
| WO | WO 02059263 A2 | * | 8/2002 |
| WO | WO 03027252 A2 | * | 4/2003 |
| WO | WO2004040000 | | 5/2004 |

OTHER PUBLICATIONS

Lee (Nature Biotech., Oct. 2006, vol. 24, No. 10, p. 1279-1284).*
Monk (British J. Pharm., 2007, vol. 152, p. 429-448).*
Sato (Thrombosis and Haemostasis, 1999, vol. 82, No. 2, p. 865-869).*
Roebroek (Methods in Molecular Biology, 2003, vol. 209, 187-200).*
Homanics (2002, Methods in Alcohol related neuroscience research, Editor, Liu, Yuan, p. 31-61).*
Lester (Current Opin. Drug Discovery and Development, 2003, vol. 6, No. 5, p. 633-639).*
Champtiaux (Current Drug Targets—CNS & Neurological Disorders, 2002, vol. 1, p. 319-330).*
Girardi (J. Clin. Invest., Dec. 2003, vol. 112, No. 11, p. 1644-1654).*
Wong (IDrugs, 1999, vol. 2, p. 686-693).*
Cain (Biochemical Pharm., 2001, vol. 61, No. 12, p. 1571-1579).*
Woodruff (Inflammation, 2001, vol. 25, No. 3, p. 171-177).*
Drago (Cellular and molecular life sciences, Jul. 2003, vol. 60, p. 1267-1280).*
Gu (Developmental Cell, Jul. 2003, vol. 5, p. 45-57).*
Woodruff (Arthritis and Rheumatism, Sep. 2002, vol. 46, No. 9, p. 2476-2485).*
Kedmi, Society for Neurosci. Abstract Viewer and Itinerary Planner, 2003, vol. 2003, pp Abstract No. 533.12.*
Wang, Blood, 2002, vol. 11, No1. 11, Abstract 2681.*
Rozmahel (Human Mol. Genetics, 1997, vol. 6, No1. 7, p. 1153-1162).*
Gerard, N. P. et al. Human chemotaxis receptor genes cluster at 19q13.3-13.4. characterization of the human C5a receptor gene. Biochemistry (1993), 32: 1243-1250.
Höpken, U.E. et al. The C5a chemoattractant receptor mediates mucosal defence to infection, Nature (1996), 383: 86-89.
Heller et al. Selection of a C5a receptor antagonist from phage libraries attenuating the inflammatory response in immune complex disease and ischemia/reperfusion injury. The Journal of Immunology (1999) 163: 985-994.
Köhl, J. et al. Anaphylatoxins and infectious and non-infectious inflammatory diseases. Molecular Immunology (2001) 38: 175-187.
Berman et al. "Lymphocyte motility and lymphocyte chemoattractant factors." Immunol. Invest. (1988), 17: 625-677.
Kavanaugh et al. "Role of CD11/CD18 in adhesion and transendothelial migration of T cells," J. Immunol., (1991) 146: 4149-4156.
Prosser, et al., Targeted replacement of rodent CCR2 with the human orthologue CCR2B: A mouse model for in vivo analysis of human target-selective small molecule MCP-1 receptor antagonists, Drug Development Research, vol. 55 Issue 4, pp. 197-209, Published Online: Jun. 21, 2002.
Hugli et al., The active site of human C4a anaphylatoxin. Mol. Immunol. 1983;20:637-45.
Lienenklaus et al., Human anaphylatoxin C4a is a potent agonist of the guinea pig but not the human C3a receptor. J. Immunol. 1998;161:2089-93.
Mukherjee et al., The role of complement anaphylatoxin C5a in neurodegradation: Implications in Alzheimer's Disease. J. Neuroimmun. 2000;105(2)124-30. Muller, Ten years of gene targeting: targeted mouse mutants, from vector design to phenotype analysis. Mech. Dev. 1999;82:3-21.
Woodruff et al., Species dependence for binding of small molecule agonist and antagonists to the C5a receptor on polymorphonuclear leukocytes. Inflammation 2001;25:171-7.
Dymecki, Susan M., Flp recombinase promotes site-specific DNA recombination in embryonic stem cells and transgenic mice., Proc Natl Acad Sci U S A. Jun. 11, 1996;93(12):6191-6196.
Takeuchi,et al., Flp recombinase transgenic mice of C57BL/6 strain for conditional gene targeting., Biochem Biophys Res Commun. May 10, 2002;293(3):953-957.
Layton et al., "Cross-species Receptor Binding Characteristics of Human and Mouse Leukemia Inhibitory Factor Suggest a Complex Binding Interaction," J Biol. Chem., 1994, 269(25), 17048-17055.

(Continued)

*Primary Examiner* — Michael C. Wilson
(74) *Attorney, Agent, or Firm* — Carol L. Francis; Bozicevic, Field & Francis LLP

(57) ABSTRACT

The present invention relates to transgenic non-human mammals comprising a polynucleotide encoding a human or humanized C5aR. The invention also relates to use of the transgenic non-human mammals in methods of screening for agonists, inverse agonists and antagonists of human C5aR and for testing efficacy of C5aR agonists, inverse agonists and antagonists in various animal models of disease.

17 Claims, 8 Drawing Sheets

OTHER PUBLICATIONS

Mosmann et al., "Species-specificity of T cell stimulating activities of IL 2 and BSF-1 (IL 4): comparison of normal and recombinant, mouse and human IL 2 and BSF-1 (IL 4)," J. Immunol., 1987, 138, 1813-1816.

Liu et al., "The α chain of the IL-2 receptor determines the species specificity of high-affinity IL-2 binding," Cytokine, 1996, 8(8), 613-621.

Höpken et al., "The C5a chemoattractant receptor mediates mucosal defence to infection," Letters to Nature, 1996, 383, 86-89.

Labarca et al., "Point mutant mice with hypersensitive α4 nicotinic receptors show dopaminergic deficits and increased anxiety," PNAS, 2001, 98(5), 2786-2791.

Smith et al., "Species Specificity of Human and Murine Tumor Necrosos factor," J. Biol. Chem., 1986, 261(32), 14871-14874.

* cited by examiner

Mouse/Human Fusion Locus (not to scale)

SEQUENCE LISTING

```
<160> NUMBER OF SEQ ID NOS: 7

<210> SEQ ID NO 1
<211> LENGTH: 21005
<212> TYPE: DNA
<213> ORGANISM: Mus musculus
<220> FEATURE:
<221> NAME/KEY: misc_feature
```

```
<222> LOCATION: (5484)..(5484)
<223> OTHER INFORMATION: n = a number of unknown nucleotides, data
      available from the mouse locus suggests about 626 nucleotides in
      length
<220> FEATURE:
<221> NAME/KEY: misc_feature
<222> LOCATION: (7392)..(7392)
<223> OTHER INFORMATION: n = a number of unknown nucleotides, data
      available from the mouse locus suggests about 100 nucleotides in
      length
<220> FEATURE:
<221> NAME/KEY: misc_feature
<222> LOCATION: (9861)..(9861)
<223> OTHER INFORMATION: n = a number of unknown nucleotides, data
      available from the mouse locus suggests about 233 nucleotides in
      length

<400> SEQUENCE: 1
tttattttta ttttttaaa aaattggtcc ttcctatgca ggtggcctgg aattttaat      60 cctcctgctt ttgtccaagt aatagaatta caggcatgta taattgtgcc taacctgagc   120
caattttgtc tttgctaaaa agcacaggtt ctcaacctgt gggtcctgac ccctggggg    180 agggtgtcac atctcagata tcttgtatat ctgatattta cattacagtt atgaagtaac   240
aatgaaatgc ttttgtggtt gggggtcacc acaatatgtg gaaccaactg ttttcagggt   300
cacagtgtca ggaaggttga gagccactgc tacaaaggat ctcacaaagc ctactctgga   360
ttagaagtta ctgtgcagcc aggaggatgg ctttgaactt attctcctgc ctcagccgcc   420
tgggtgctgg ggtcggatgc agcactacat caggttttat gcggtgctgg aatggtatc    480 cagggctttg cacatgctag gcaagtgttt aaccaaccaa gccatgatcc cagcatgctt   540
tgctttatta tttgagacag gtcctgttct gcagcccagg gtgatcctcc tgccccagtc   600
tcctgagtgc tagcattgag ttaacacatc tccctaaccc ccttaagaga aacgccaag    660 accttggcca tctcttcagc cctctgtgtg cttcttgct ataaaagcca ccaggctggg    720
gagctgtggt cattatttct gtcatgtaga accccagaa actccaaaac ttccttcaga    780
agaggtaggc tcctcctcag attggggaac gaggccagga aaagcagctg cgtcccaaa    840 agtgaagaag tcctggaaat tgccttttcc ccttctgggg ccagagactt ccttccttt    900 ccaagttgac atctctcccc tggctggttg gtactgggtg gtgctgaggg tgtactgggt   960
aagcaccggt ggagggagcc tcagctagga tggtcagtga gtgaccaatg agcacctcca  1020
ggagacaaga cagtcatttc ctctcagttg cctgcatctc ttcttgaggg tttaaaaggc  1080
acagcctggg tgacagggac cttcaggcat ccgtcgctgg ttaccacaga acccaggagg  1140
agccaggaca tggtgagtgg attcctctcc ctgtctgact ttctttgccc atttctagct  1200
cctttcccat cctgagctca cactctgaga tgggatgtgg ccaacggact aagggggattt 1260 atgggaacca cggcggcctc accaagatgt aggctcaaga aggttcttca ggacaggaga  1320
ccctggagtc agctctcctc actgaagagt tctagaagtt gggcatgttc atttacactt   1380
gtaatctgag ccctcaagag gccggggcag gatgctgcag tcaaggctac atagtgactt   1440
ttaggctagt gtgagctaca ctatgagata ctgtgttcag agacaaatgg gctggaggta   1500
gagatcaggt gtgagagtgc tctgtgggag agctggaagc catgggtcca atgaccagca   1560
cctcgtacag ctgggtggga gtgattggaa attcaatctt acatagtaat tttgaggtta   1620
acctgggcta cactacatga gaccctactt cagaaaagca agaacaaaaa aataatttta   1680
caaactagcc aaggtggtgg ctcaaacctg ctatcctggc tcctagcagg aggtttgaga   1740
tttggggcga gcctaggcaa ctttgttgag actttgtctc aaagactaaa agcaaaacaa   1800
aacaaaaact caaacagtgt gaataaagga aggaagaatg aaacaattgc agaaacctgt   1860
```

```
tgggattgta gctcactgcc tagcctgagt gtggcccagg gttccgtctc ctacgctgag    1920
tctaaaacta ccaagcagag actgggtgct gtgacgcaca cctttaatc ccgcactcag    1980 gaggcagaat cgggaggttc tctgtgagtt cgaggccagc ctggtaaaca tgtaaagaag    2040
tctaaggaag gtcaatgttg agagtcttga cagccagttt gaaagaacgc ccattcccag    2100
aaaagttaga ggaagcccag atgggagcac tgatggcctg ggtccttctg tggttaatgg    2160
ccatgaccct ctaggcaggt ccctctccat gcctgggacc tgacgttgag gcatggtgct    2220
agaccagcgg cgacttggcc ccactgtaac agaggatacg gtcttgcttc atccacacaa    2280
aagaggaaac ggaaaacttg atgacaggga gggtacacgc tttcttcatc cttcttctgt    2340
cccatccaat cctgtgtctg ccccgagcaa ttggggtttc cagaacaggg tgggttcttt    2400
ttcctttcta cacaacgttt ctgaagacga agtcacttta ttgaccaccc gaactgtaga    2460
gtccctgatt tgggctgggg cgtgactgag ttttttgttt tttgtttgtt tgtttgtttg    2520
ttttaaatac tggaataggc tgtcagtatc tttttttttt tttaagattt atttattata    2580
tataagtaca ctgtagctgt cttcagacac tccagaagat ggcatcagat cttgttacag    2640
atggttgtga gctaccatgt ggttgctggg atttgaactc cagaccttcg gaagagcagt    2700
cgggtgctct tacccactga gccaactcac cagccctttt tttttttttt tttttttttt    2760 tttttttaa agatttactt atttatata tgtgagtagt attgtctctt cagagacacc    2820
agaagagggc atcagaccca attacagatg gttattagcc accatgtggt tgctgggaat    2880
tgaactcggg acctttggaa gagcagtcag agctctaaac cgctgaacca tctctgcagc    2940
ccgtgactgg attcttaggc cagtagtcta tggctaagct atgcccctca cccctcactg    3000
ggggattcta ggcaggggct ctaccactga gccacactcc cagcccctca ctggggatt    3060 ctaggcaggg gctctaccac tgagccacgc cccagcccc tcactgggg attctaggca    3120 ggggctctac aacatttcag tccttgatct tttaagacag gatgtcacta tgtagcccaa    3180
tggtctaaat cacatgatta tcctcaggct ccctggtgct gggatcacag gcatatacca    3240
ccgtggctag cccctaaaca taattttct tttgaatgaa taattttttt cttttggttt    3300
ttcaagatag gatttctctg tgtagccttg gctgccctgg aacttgctct ataaaccagc    3360
ctggcttcaa actcacagat cctcctgcct tacctcctg agtgctggga ttaaaggcat    3420
gtgccatcac tgcctagctt tgaatgaata cttttttta atattgtgaa taggcattta    3480
ctgagtgctt attgtatgct agtcctcttg ctaagcactt tagatttact acatagcaaa    3540
ctatcaataa aggagctgta gaatatccat gtatttcaag ggcaacacag cctttgaaca    3600
gacatatact atcccaatgg cattccacgc attaggcggt ataacctttt aaagagaagg    3660
ctcttgggat tcggcccac ccctgctctt gctgatagt tttgggaggc tttctaacta    3720
acctagagcc ccacttttta aaatctgtag agtgggtgtg gccatagtag cagcccaatg    3780
agggttgcat gtgttaaatg aagaaaagag cagttgaaag cccctcacaa gtggcccata    3840
cctgtaatcc cagcactcag gagaaagagg ccctgtctca aagaaaata caaaaagcat    3900 gtaaacttat ggaccaggct aattatttta ttttgttttt ttaaaaaga tttatttatt    3960 tatttattac atgtaagtac actgtagctg tcttcagaca ctccagaaga gggagtcaga    4020
tctccttacg aatggttgtg agccaccatg tggttgctgg gatttgaact aaggaccttc    4080
agaagagcag tcaggtgttc ttacacgctg agccatcgca ccagcccag gctaattatt    4140 gttattttga aataggttct catgtagata aggctgaacc tagaactcac tatgtagcca    4200
aggatagctt tgacttcctg tcctcctgct ccacctctgg tctctctctc tcgatatata    4260
```

```
cacacatata tgttcatttt atatattata ttgtataata gtttatagtc ttcttttttt    4320
cttttttttt ttttttttttg ggttttcaag acagggtttc tctgtgtagc cctggctgtc    4380
ctggaactca ctctgtagac caggctggcc tcgaactcag aaatccgcct gcctctgcct    4440
cccgagtgct gggattaaag gcgtgtgcca ccacgcccgg ctatagttca tattctttaa    4500
gcaactattt ttatatcatt tatttatttg tcttacaaga tttgttttta attgtgtgta    4560
cgcttttgag tctgtctgtc acacgcgtgc agatgccctc agaggacaga aggtgttgga    4620
ttttcggagc tggagtttca ggcagttgtg agatcccctt gggtgctgag aagtgaacac    4680
atgtcctctg cggaagctga cagtgctctt cattgctgaa ccatctctcc acttccttct    4740
tagtcttttt tttctcaatt gttttttctcc ttaaaaaata ttttgacctt atgattagtt    4800
gagtccacag acatggacac tgtgtatacg gagggacaat gacatcttct ataatagttc    4860
aaattatgta tgcatataat atgttacata tattgtattc cacatccaag aaccatataa    4920
acaggagaaa gtgctctctc tctctctctc tctctctctt aaagatttat ttatttgtta    4980
tatgtaagta cactgtagct gtcttcagtc actccagaag agggcatcag atctcattat    5040
ggatggttgt gagccaccaa gtggttgctg ggatttgaac tcaggacttt ccaagagcgg    5100
tcagtgctct tacctgctga gccattctcc agcccaggag aaaactctct taattcccga    5160
gtcccagtcc cttccttaga ggcagccact actgtcagta tgtgaggcta gtctgtatgt    5220
acacgtgaat ggacacacac acattcatgc acatgttgtg catccttcct tctacaggta    5280
atatacattg tgcattgtcc actgctattt cctattttaa acaaagtttc cctagatatc    5340
aaagaccttt ctgtatcatt tcattaacaa ctaccttatt cttttaaaaa ctgcatagtg    5400
ctttgttgcc tagaggctat tactaagtta ctcagtccct tttggtcagt tcaaaatatc    5460
attatcatct cctcctctgc ctcntgtatc tggaagcccc aggaaaccac agagtttacg    5520
atcagcatct ttttctctgc ctcatgaagt cacgaaaagg acagggtgag atcatgtcag    5580
gaagcaagaa aggagaaggt cagccggcaa ggatgagaga tggggttaga gaggcccgtg    5640
tcagaagtct gagtcattgt agtaaggatg gtgagatctg cagatgccag gagaagcatt    5700
ccaccctgtc tggggccttg agaatacccca gagggcaggc tgtgaggttt cctatagggc    5760
ccagaattaa tcctcaagtg acctgagcat gggaccctgg ggatgtgggg atgcccagag    5820
taacaagtag aaagatacag aactgagggt gagccagagt gaaatgagtg gctgggtcct    5880
gggtctgtct gtctgtctgt ctgtctgtct ctctctagct ttcttttttgt ttttctctgt    5940
gtagccctgg ctgtcctaga actcactcta taaacccggc tgacctcaaa ctcagagatc    6000
tgtcctcccc tgccacccgt gctgggattg aaggtgtgca tcacatcacc accctcctgc    6060
ttgaaatatt tttaaattat agaaaagtgt gaggctagta caagaagttt atttatcttc    6120
ttttgttgtc gttgttattt attattactg agatggggtc tcgctatgta gctcaggctg    6180
acactcaatg taatgcatag cccaggctgg tctgggcgc cacatcttcc tgttcagcct    6240
cctcagtgtt ggcattacag gcgagcatta ccataaattc ttgtgtttcc tcccaagag    6300
tccccacatg cagtctatgg tgtatatatg tttacccatg tatatactta taaatctttg    6360
tatgtatcta tgtttctgtt tctataaaca tatcagttta gctgcatatc gacatatctg    6420
tttttctatc tgtcaatata gctatcaatt atgctccatc cattgtttct ctaccattca    6480
tctctagcta ttcatcatct acccaggcat tttctattct tctattagtt tagcctggtc    6540
ttgaacccccc aacctagctg aggatagctc ttttttttttt ttttataatg gtactgaagt    6600
ttatttttttt taaagattta tttatttatt acatgtaagt acactgtagc tgtcttcaga    6660
```

```
cacaccagaa gagggcgtca gatctcgtta cagatggttg tgagccacca tgtggttgct    6720
gggatttgaa ctctggacct tcggaagagc agtcgggtgc tcttacccac tgagccatct    6780
caccagccct gaggatagct cttaactctt gatcttcttg cctccaccac atagattcag    6840
gggttacagg tgcactaccg tgtccagtct atgtagcact ggggatggaa cccaagggtt    6900
catacatgat aaatgagcac tctacaagat gagctatgtt cctaacccat ctgcctgtct    6960
ttctatcacc tatgtcccat ccgttgatct ataaatcttt ttattcatct ttcacccacc    7020
cacccaacca ttcacccatt cattcttagt aaccaaggct ggtcttgaac tcttgatttt    7080
cccacccgag tcttcccagt cctgagatga tacaagtgca catcaccata cccgtgtcaa    7140
aatctacttc taattcttat ttctgttttt aaaagaaaaa gttatctgtt ttatgtatat    7200
atgtgtctgt tgagtgtata tatgtgcacc aagtgcctac aggagcctgc aaagatcagt    7260
tgtcagattc tgccattgga gttctaaaca gttgcgagct gtcacaactc tggtcctcta    7320
caggagcagc aactgctctt aactggtgac ccatctcttc taatttctct ctctctctct    7380
ctctctctct cncctctctc tctctcccte cctccctccc tctcttcctt ccttcctccc    7440
ttccttcccc cctcccttcc ttccttcctt cattccttcc ttttgttttt tgtttgtttg    7500
ttttttttta attaggtatt ttcctcattt acattttcaa tgctatccca aggtcccccc    7560
atcccacccc cccaatccc ctaaccaccc actcccccctt tttggccctg gcgttcccct    7620
gtactggggc atataaagtt tgcaagtcca atgggcctct ttttgcagtg atggccgact    7680
aggccatctt ttgatacata tgcagctaga gacaagagct ccagggtact ggttagttca    7740
tattgttgtt ccacctatag ggttgcagtt cccttagct ccttgggtaa tttctctagc    7800
tcctccattg ggggccgtgt gatccatcca atagctgact gtgatcatcc acttctgtgt    7860
tttgtttgtt tttttgagac agggtttcat cgtgtagccc tggctgtcct ggaactcact    7920
ctggagacca ggctggcctc gaacacacag gatctacct acctctgcct cccaagtgct    7980
gggattaaag gcatgctcta ccaccacctg gctagttctt atttcttatt ttgccttttg    8040
ctggccccaa atactttgcc tccacttcca attgtaagtc ccaaaactta gggtttggaa    8100
aatgggtggc ttgctagact gtcaaggaga taatgaagga agaaagggag gctcagagcc    8160
agagaaattt gcaaaggaac ctgtatgccc cataggtctg gatcacaggg gataactcca    8220
aagccagtat ccaaaggaca gcctatcctc agctggggt ggagtctttg cctgcttccc    8280
gcctatacta aaatgtcgaa ctatttttc tctttctctc tctctctttc tattttttct    8340
tttaaagatt tatttattta ttttatgtat atgagtacac tagggcatta gatctcatta    8400
cagatggttg tgagccacca tgtgattgct ggaatttaaa ctcaggacct ctaggagagc    8460
atccagtgct cttaacctct gagccatctc tcagccctct ggttttttgt tttgttttgt    8520
tttgtttttt tgttttttta aagacagtat ctcattgtct tgttagcag ctctgtcctg    8580 tcctagaact cactatgccc aacacactga cctcaaatac atgcttatcc acctggctct    8640
gcctcccaaa tgctgggatt aaacatgtgt accaccacta cctggcatct ctgtccatca    8700
ttttaatcaa agagaaaaat gtataaaact ttttcttaag tagcccagac tggtaatgag    8760
gatcactgtg catctgagga tgagtctgtt gcctctgtct cccagattct ggggtgggag    8820
tcaccatttc tagtttaatg ttgtgctggg tttggagtct gtggcttcat gctttgagac    8880
tggtttcctg taaggcaggc gatcattgaa tgcttcccca ccctgcctcc tgttactgaa    8940
tgtcaggatt gtagccatga gccgccatgc ccgctttaat ataagatcat ttaaagcagt    9000
agttctcaat ctgttgtcag agagtagcaa gcttacagtc aggaagtagc aacaaaagtc    9060
```

```
attttatggc tgggggtcac cacaacatga ggaactgtgt taaaggtctc agccttcgga    9120
aggttgagaa ggaaacctca aacccacaga tatcggtcac agttctcaaa ggaccacatt    9180
gcccaatatg tttatacacc atggtcacat ttccagccca ccgaggacac caggataaag    9240
cttcactgcc aacaatgagg tgtttcaaaa ttagatgtca ttgtcctgtc tttataccaa    9300
ctttgggttt tagtccaaat tcagggcata cacatctata attctagcac acaggaggta    9360
gaggcagggg gatcagtagt ttatcatctt gagctacata gtgagttttg ggactagcct    9420
ggtatacagt ggattctgtc aaaaaactaa atgacaaaga agtaacaaca acaacaacaa    9480
aataataata ataataataa taataataat aataataata atattattat tattattatt    9540
attattatta ttattattat tattatttgt gtgtgtgtgt agtgtctgga cataggtc      9600 aagctgagct tgaactcagg acaatcctca tacactgttt tgagctcttt atatcactgg    9660
gagctggaga gtgtagctca ggagctcaac agtacctgcc agagtgacag gagttcagtt    9720
ccaagcacct atgtagagta tgctcacaac cagatgtaat tccaaagtgt tcaatgccct    9780
cttctagcct cccagggcac cctcctctct ctctctctct ctcctctc tctctctctc     9840 tctctctctc tctctctctc nccccccata cagtaccaat ggtaagatgg tttagcaggt    9900
aatcgcccaa gcctggagac ctgagttcta tcttaggacc cacataaagg ttaagggaga    9960
gaacgcagtg cacaaagtta tcccctggct ttcacatgtg tgttatggca tgcacatgca   10020
tacatacata catgcataca tacatacata catacataca tacatacata gacagtgaca   10080
aattaaaata atacctcatt ggtcagtcac tgcaccccctt taatcccagc actcagaagc   10140
cagaggcagt tggaactctg taagagtgga gccagcctgg tctacagagt gagacttttt   10200
cttttttctt tttttttta aagatttatt catttattat acgtaagtac actgtagctg    10260
tcttcagaca ctccagaaga gggagtcaga tctcgttacg gatggttgtg agccaccatg   10320
tggttgctgg gatttaaact cctgaccttc ggaagagcag tcggttgctc ttacccactg   10380
agccatctca ccagccccga gatttttcct catcacctcc ctaccccaat ccatatactt   10440
gattaaagcc caggtctgga gagccatgcc tgtagtctca gcattgggca gctgaagtag   10500
atggaccacc atgatttcag tttatcctgg gcttcagagt gagtttaaga ccagtctggg   10560
taatttaaca gagaacctgt ctcaaaataa aatctacaaa ctatactagt tttataggtg   10620
ttcagcatcc cttggtagag ttgagactca gaaagacggg caatgcctcc atccctggg    10680 aatgtgtcta ccaactcaca caatctacct gtttgatttg cttaggaccc catagataac   10740
agcagctttg aaatcaacta tgatcactat ggaaccatgg atcctaacat acctgcggat   10800
ggcattcacc tcccgaagcg gcaacctggg gatgttgcag cccttatcat ctactcggtg   10860
gtgttcctgg tgggagtacc tgggaatgcc ctggtggtgt gggtgacagc cttcgaggcc   10920
agacgggccg tcaacgccat ctggtttctg aatctggcgg tggccgacct cctctcgtgc   10980
ttggcactgc ctgtcctgtt cacgaccgtt ttaaatcata actactggta ctttgatgcc   11040
accgcctgta tagtcctgcc ctcgctcatc ctgctcaaca tgtacgccag tatcctgctg   11100
ctggctacca ttagtgccga ccgtttcctg ctggtgttca gcccatctg gtgtcagaag   11160 gtccgcggga ctggcctggc atggatggcc tgtggagtgg cctgggtctt agcattgctc   11220
ctcaccattc catccttcgt gtaccgggag gcatataagg acttctactc agagcacact   11280
gtatgtggta ttaactatgg tggggtagc ttccccaaag agaaggctgt ggccatcctg   11340
cggctgatgt tgggttttgt gttgcctctg ctcactctaa acatctgcta caccttcctc   11400
ctgctccgga cctggagtcg caaggccacg cgctccacca agacgctcaa agtggtgatg   11460
```

```
gctgtggtca tctgtttctt tatcttctgg ctgccctatc aggtgaccgg ggtgatgata    11520
gcgtggctgc cccgtcctc gcccaccttg aagagggtgg agaagctgaa ctccctgtgc     11580
gtgtccctgg cctacatcaa ctgctgtgtt aaccctatca tctacgtcat ggctggccag    11640
ggtttccatg gacgactcct aaggtctctc cccagcatca tacgaaacgc tctctctgag    11700
gattcagtgg gcagggatag caagactttc actccgtcca cgacggacac ctcaacccgg    11760
aagagtcagg cggtgtagag gagaagccac aactggccta gctgctcctt ttccagccct    11820
cctaccccct cctcttcttc ctcctcctgc ctctcctcct tccttccttc cttctctttg    11880
catgtttaat tttctgcaat tctctaagtt gctctgacta gccttgagcc caggatcctc    11940
atgaaggctg agattataaa tataaattcc tttgatgaaa agcatcacat taagatagta    12000
ctcggctttt tttctaaggc ttttttttt tttcttggct acgttccca cctgcagtgg     12060 ctaggcagat acacctaatg atgacctcca ggggttggat aacagagaac aagagaattt    12120
cctggccttc ttcttcctct cttcctcttc ttttcctc ctcctccttc ttctcctcct      12180
cctccctttt ttttttatg gttctggtct gaacccaggt ctcaatggaa cccagggctt     12240
atggatatat cacataagca agctacagcc ccaaacccca ggcaaccagt atccaccac     12300 cctttatttc ttttctatgt ttgattttt tttttttga gacaaggtct catgtagggt      12360
agtctggcct tgaactccag atcctcctgt gaccatctcc caagtgtcgt gactgtagac    12420
ctgtgctgtt gtgtccgacc tatcctttat ttctacaatt ttgtgttttc aggaatggta    12480
tttaatggaa cccaacatat ccaagctttg taaaaacaac tatgcatggc ttacttgata    12540 aattttttt ttttaaaaag gtacagaaat gtgttgttta acttttttaaa agcacgtatt    12600 tatttatttt gtgggggtg aggggtggt gctgggcaaa tgtcatggta tatgtgtgga     12660
ggtcagagga caacctgttg aaattggttc tctcattgca accatgaagg tcctcatgga    12720
atcgaaccca ggtcatcata cttggcagca aacacctta cctgctgagt cacatcactg     12780
gccagaggtg tcctgtctta taatgcgttc tttcagctta atgaatgtgt gtgcatgagt    12840
gtatgtgttg gctagaaaat atgtacagat caacaccaga agtatcatgc aagcatggga    12900
atggttttga atttcctggt caaattaaaa atgtgaaaga agacctgggt gtggtggcgc    12960
aaacctatat cccagcatgt gggaggttca ggggccagaa ttgagtttta gaacccagcc    13020
tggcttaccc agggagactg tctcatgaga tccaaataaa cagtatatga tggaaaacac    13080
tggagtttag ctctgctagg ccctctcttc ttcccagtgg atatgtgacc actggttgtc    13140
acatatcaca gacccagcct acctgtgttc tgctattcac actttctata tgatgacact    13200
aacctcactg aattttttaca ggctccatgc cttggcattt attatttatg tatttattta   13260
ttttgagaca ggatctcttt acatagccct agctgtcctg gaactcacta tgtgaaccag    13320
gctggcctag aactcacaga gatgggcctg cctccatctc ctgagtgcta ggattaaaga    13380
catgagccac cacatccagc tttattctat gttttgtatg gcctctatga gtttgaaaca    13440
tttaatcaat tagttagtta attaattaat atatgagatg ggatctcatg tagcccaggc    13500
tagccttaag ctggttttac agctgaggtg ggattatagg tagtcctcct gactcccagt    13560
tgtctccctc ttgtggcttt tctcattatc ggtcacatct gtattgccac agctgagctt    13620
ctcacccact gacccatgcc ccagctgtcc caagaacctc ttcctcccct tgcttttcca    13680
ttccaggaaa aaccacactg gcaacctgct cacccaggcc ctttcagctg ccccatcaca    13740
gacccagccc tcccttctta ccacacaccc ggctctacat cctgcccccc cccccgcac    13800 ccccccgc ctccttcatg cctctcccctt cccttgatct cctggttgcc cagcacctct     13860
```

```
tccaaggacc atcctgctcc catcctgtct tcttgccagg tgtcccctcc ttaagggagt    13920
cccctgtgac agccctcagt ttcccataag caccctacca tcaatctttt tctctggctg    13980
cgattgagct tcctggttca gggagtaagt agtaggtagg gattcacctc cttctggcct    14040
tgctgtaatg agatgctgtt ttaagggttg ggctgagggc tggggctagg gggtggggtg    14100
gggttagaaa gacggatcag tgattaagag catttgatgt tcttttagag cagcggttct    14160
caacctctgg gtctcaacct ctttggcaaa cttctgtttc caaattattt acattccgat    14220
tcataactag caaaattaca gttttgaagt agaaatgaaa ataactttat ggtttggggg    14280
gacactgcag agtgaggaac tgtatttaag ggtcataggt cgtagcatca tgaaggttga    14340
gaactactgt tttaaaggat tagttcagtt cccagcatcc acatagtgtc tcctaatgat    14400
ttgtaatggc tgccttggac accaagccca cacatgctgg acatacatgc aagcaaaaca    14460
cccatacata taaaattata tataatatgt aagctgggcc caggatacag tgtttcagtt    14520
cagtaggtag catgctggcc taacacgcac aagcctctgg ttcagtcccc tgcactgaat    14580
aaaatctcca atagtggttg ggtgtggtgg tacatgcatt taattccagc actccagaca    14640
cagatgcagg cagacctctg ggagtttgag gccagctact tagtgagctc caggtcagtc    14700
caagtgagac ttggttttcaa aataaaacaa atatatacac acaaagaaac taaatctgca    14760
tggtggattt aggaggtaga ggcaggaggc tcatctagtc aaggagagtt tgtggctagc    14820
ctgggctaca tgaggccatt ctgggctaca tgagcctctg tctgaaaaca caaacaaaaa    14880
caaatgaaca aacaaacaaa caacaacaaa aatcccagcc aggcttggta acaagcattt    14940
gggagacggc cataggtgga cctccgtgag ttcaggctgc agagagaggc cagtttaaaa    15000
ccaaaacgag acaaaaaggg atgctcagtg gtttaagagc attggctgct gctcctccag    15060
gggactgagg tttccttccc agaacccaca gggcagctca caactgtctg tagctccagt    15120
tccaggggag ctgatgcagt ttccttgcct ccacaggcat ggtgtgtagc acgcagatat    15180
acagacaaac cactcatgca ccaaaggcaa aaataaatta atctaaaaga aaggaaggaa    15240
ggaaggaagg aaggaaggaa ggaaggaaga aagaaagaaa gaaagaaaga aagaaagaaa    15300
gaaagaaaga aagagaaaga aagacaggaa ggaaggaagg aaggaaggaa ggaaggaagg    15360
aaggaaggaa ggaaggaagg aattggacat acagcaggtg gtggtcatgt tgagagaccc    15420
ccaccccagg tgactcccag gcaggtcagg gttaagcaac gcagctcaaa acagaagttt    15480
gcagagtcca ggggattgcc aaatgtgtgg cctgtggaat ctgcttatgt caacagggtt    15540 ggaagggaa gtgagcagga aaggaagtgg gctgagagct tggcggactc tagtgtgttc    15600
tttctcctcc cccagcccca gccttctgga cccttgggtc ttacacacct atctgttctt    15660
cagatgcagg gctccaaggc ctggggccag agccgccttc ccttgtaacg gtgacctccg    15720
ggagctcaca tccaggaagc tgttacattg cagtagagtc ttctgggatg aaatatgagg    15780
ggctgggaga cgggtcagtg agtaaagtgt ttgccattta aacataagga tatgcgttcc    15840
agcccaggct atggatttgc ctggtacaga ggcacggtgg ttgtgtttg taacctcagc    15900 acgggagagt gagacagatg gatctctagg gcttgctgac cagcaggcct gggttaatca    15960
gtgagcatct agagcaagtt gagagccttg gtctctaaac acaaggtgga aggaaaggga    16020
gggccctgga gaggtggttc ataggtaccg ctctcagcag caagcactct cacctgagga    16080
gccctagccc tagctctact actgagccac actcccagcc cctcattggt gagttcttgg    16140
ttctgttgag ccaggccccc aatccttttgc tggaggattc taggcaaata tcctaacact    16200
gagctgtgca ctgctccaga cctttttatca tcttggcaca tctgttgacc aggtaagtct    16260
```

```
cccatgttga ggtgtggaga acactgaggc ctttcaggat gagagagaga gaggagaggc    16320
ctgcatcaca gaatctgtag tgccttgacc cagaagcaat ttcctctaac aacatgactt    16380
tatgctctaa atatcaacag aagaatttgt gaccgcatcc ttctcagcct taagcaaggc    16440
tcagagagaa agacgaccat caggaactgc tgagtgacga gagtccatgt cagggttgag    16500
gccatgtcct gctcggtgtc ctaagcctgc accatgctgt aggtgtatag tttaagacag    16560
tgtactctag ggcacacttt aattcccaca attgggaagc tgaggaaagc aaatctgtga    16620
gtttgaagtc actctggcct acgtgagacc ctgtctcaaa cccaacccaa cccaaatcaa    16680
accaaaccaa acccagccac tatagccaac ttcttttttg ttcttgtcat tactactact    16740
actacaaata ataataataa atatctaata ataattttca ctttaaatat ctgtgcacat    16800
gggcctgtga gagtcacagt ttgtatttga aggtcagagg ctagccttaa ttctagagct    16860
ttcctttcta ctttgagaca gagtctcttg ttgcttgtaa tggcaaaggc cagctggccc    16920
acgtttccag ggattttgac tccctggctg tcttcctttc tgaacgctgg catcacatac    16980
atatactact gaatgtggct attatatggg ttccagaact tcaacctcag gtccccatgc    17040
ttgtgtgacg agcacattcc ccaccaatcc acccatgggg accggacaga tctctcccgt    17100
gagctccccc ttgcctctgc ctccggagtg ctggagtgac aagcatgttc tcctatgcct    17160
gctgtcttcc cattttacag gtaaaaaaac cagaggccca gaaaggggac aggatttgct    17220
tattttgggg catgtggggg tttgagacag ggtttctcta tgtagtcctg gctgtctctc    17280
tgtgactctt ggctggcctc gaactcagag acctgtctga gtgctgtgat caaaggtgtg    17340
cgccaccact gcatgacagg acttgcattt tatgttcccc ggaaacctca ggccctgggc    17400
tcagcttctt gatcttttctg aggagggttc attctgggct atcatcctca caacatttga    17460
ggaaggaaag atctttaaga gtctgtggct ggcaggaatg agaggcagag aacagcgcag    17520
ccggtcagtg gagggttagc aggccgctgg tgattactgc agaatcttag gggtcccttta    17580
gtgccaaggg tgggtgggaa gtggtttcag agatagccct ccagaccttg ctgttcaaag    17640
cccacacacc tctggcttcc aggaagctga tagtagtgag gctgcgggtg gaggcacaca    17700
ctttcggctt ttccgacctt tctgtctgtg ggttaatttg tgactcacgg ggaggaagaa    17760
aagacaacta tttccctggg gctagcggag gccacgcctg ttttttcctgg ttaagaaggt    17820
tgcgcagggt cctcagagaa tcccatagga tctggggaag ggttgcattg ctgagactca    17880
ggcccgctac tgtccctggt ggagagactc tgggcttcct tgcggctgct gaggtctgct    17940
gtgcttgtgc attcggccaa tttgggacca gtcagaagag aggtgaggaa gggaggcata    18000
aaggaggttg cgagaagggg tggagaggct cataatgttt gccttagaag ctttcatttt    18060
gaaatcttgg gagtcagaat tagcattcca gattatatat gttgtatttt cctgagacaa    18120
gagctcatgc tgtccaggct gacctcaaac tcactatgta gttgaggtga tctcgaacac    18180
ccgagtgtcc tgcctccacc tccagagtac agggatcatc aaacacaggt tatgtagtgc    18240
tgggagcaga gctcagggac tttggcactc taccaactga gccacacccc cagccctgaa    18300
tcatataaaa taatctgttt cattacgaca tttatattat atatgaatgt tcttgagttt    18360
tgctcaaatt caccaccatc tcttttctca tcagcttgta tgttgttgtt gttgttgtta    18420
ttattgatac aaaatatctc tacgtagctc tgactgtctt ggaattcgtt atgtagcaaa    18480
ggctggattc acagaaatcc acctccctct gcttccagag cactgggatt aaaggcatac    18540
tcctggctta tacttaaaag tggcaatttg gagctgaaga gatggctcaa tggttaagaa    18600
catgcaatgt tcttttcagag gtcctgagtt aggttctcag aacccatctt atcagtggct    18660
```

-continued

| | |
|---|---|
| tacgaacacc tgtaactcct gctctaggga gtcagatgcc ttcttctggc cccagcaggt | 18720 |
| aactgcacac atgtggccaa cacttgtgtg catagacata tgtaaaataa tggcaataat | 18780 |
| attttatgta ttgtgtatag agccaaacaa atataaatga tttactgtaa aagaaagcaa | 18840 |
| tgtcactggg tgcagaagtg tccatttgta atcccagatg agaaggcaga taagaaaaga | 18900 |
| acggtttctt ttactctctg gcccatctgt tgagccagtt ggcaaacttg aggttctgtg | 18960 |
| agatatccag tctgaaaaaa tgtggagggc tggagggtgt ggctcagtgg tagaccccct | 19020 |
| gcctagaatc ccccagtgag gggctggggg cgtggctcac agccggagcc ccttgttaag | 19080 |
| ctggaaagcg ggagatagcg cgagatagag agggggggtag acgagagag agagagcgag | 19140 |
| agagagagag agagagagag agagagagag aacatgaatt ctgggaacca tccttgtctc | 19200 |
| tctttacaga ggaaatacca taggctgata gtgactgagt acagaaactg tcccagacta | 19260 |
| ttatcagtag tagctgtgaa gggtggggtc agagatggga agagaggtag tgataacagc | 19320 |
| agttcacaca cacatacaca cacacacaca cacacacaca cacacacaca cacacacaca | 19380 |
| caaacacaca cacgagcagg cacaccctgt ctgctgtttg ctgtggacga gcactgtggc | 19440 |
| agcctgtctc catagcagat ccgctaacta cactgactat ccgcagcgct cgctctccca | 19500 |
| ggtggggtct gtgattatcc ctatacaggt acacagagat tccgcagctt gttgaaggcc | 19560 |
| acacagctat tgaagctttg agtttttgta ctcttgttat gctctatatt gcttgttttg | 19620 |
| tttgtttgtt ttgagatgag ggtcttaact tatagcccag gttggcctca aaatcatggc | 19680 |
| atttctcctg cttcagcctc tgagtgctgg ggtgacaggt gagttttgt tttgtttgt | 19740 |
| ttttaaacag gtacagttta ctttaaggaa ggaaaactac tcagaaaaat ggcttggcct | 19800 |
| catagctggc tacctggcag agctgagagt gtcccaattt ccgttctgtc cttcctgttt | 19860 |
| taacagtgtt ggccaaggct ttgggcagtg ccagacaacc cataaatagt cagatgagag | 19920 |
| ctgcaggttc cagccactcc agacatgggg ttgggtgtcc cctcccgccc aggtcctgtc | 19980 |
| cttccccgcc tgctttgtgt cttgtgtgtg tttcttaggc tttagttctt ctgtcccacc | 20040 |
| aaactggtga gctgggtcct agaggaggat gtgcacagac agagccagcc gtgactgcgg | 20100 |
| gtcagctcag ggccacgggg atacacggct gactagcttc ccagtttctc acatctgggg | 20160 |
| ccggtaaatat ttctggactc cctagggaca cgctgcaatt cagttctgtc ttcttagctg | 20220 |
| agtgatttta actaagttac tcaccctctc tctgcctctt tagctgcaga atcggcttac | 20280 |
| caagactgta tcaaaacaca gtgttgaaag gtgtttgggg ccaggccttg cacgtgcaca | 20340 |
| aaatggtgcc ctctaatatc ctaaaactat tattattatt ttattaggta attttgtgtc | 20400 |
| ttagttaggg ttttttattgc tgtgaagaga caccatgagg ggctgggggc gtgactcagt | 20460 |
| ggtagaacac ccacctaaaa ttccccaggg gcacacgcaa ctctctctct ctctctctct | 20520 |
| ctctctctct ctctctctga cagggtttct ctgtgtagcc ctggctgtcc tggaacttgc | 20580 |
| tttatagacc aggctggcct caaactcaca gagatccctc tgcctctgct ccaagtgctg | 20640 |
| gaattaagtt gtacaccacc actgcctggc taattatttc tatcttaata gtttcttttc | 20700 |
| ctgttgcttg tgatgaaata ctccacagcc agatgtggtg gcacactttt ttatcccaag | 20760 |
| acacttggga ggcagaggta ggtaaatttc tgtgagtttg gggccattct ggtctacata | 20820 |
| aaatactctt aaagggctac ttaagggaga aggtacttat tatagattat tatatattat | 20880 |
| gtcattatat attatatata atctagagaa ttaatattat aatatttcta taatacatac | 20940 |
| tatgtaatat aatattaata tcaatacaat tatattatct actattcatt atacattaat | 21000 |
| atata | 21005 |

<210> SEQ ID NO 2
<211> LENGTH: 2328
<212> TYPE: DNA
<213> ORGANISM: Homo sapiens

<400> SEQUENCE: 2

| | | | | | | |
|---|---|---|---|---|---|---|
| agggggagcc | caggagacca | gaacatggac | tccttcaatt | ataccacccc | tgattatggg | 60 |
| cactatgatg | acaaggatac | cctggacctc | aacacccctg | tggataaaac | ttctaacacg | 120 |
| ctgcgtgttc | cagacatcct | ggccttggtc | atctttgcag | tcgtcttcct | ggtgggagtg | 180 |
| ctgggcaatg | ccctggtggt | ctgggtgacg | gcattcgagg | ccaagcggac | catcaatgcc | 240 |
| atctggttcc | tcaacttggc | ggtagccgac | ttcctctcct | gcctggcgct | gccatcttg | 300 |
| ttcacgtcca | ttgtacagca | tcaccactgg | ccctttggcg | gggccgcctg | cagcatcctg | 360 |
| ccctccctca | tcctgctcaa | catgtacgcc | agcatcctgc | tcctggccac | catcagcgcc | 420 |
| gaccgctttc | tgctggtgtt | taaacccatc | tggtgccaga | acttccgagg | ggccggcttg | 480 |
| gcctggatcg | cctgtgccgt | ggcttggggt | ttagccctgc | tgctgaccat | accctccttc | 540 |
| ctgtaccggg | tggtccggga | ggagtacttt | ccaccaaagg | tgttgtgtgg | cgtggactac | 600 |
| agccacgaca | acggcggga | gcgagccgtg | gccatcgtcc | ggctggtcct | gggcttcctg | 660 |
| tggcctctac | tcacgctcac | gatttgttac | actttcatcc | tgctccggac | gtggagccgc | 720 |
| agggccacgc | ggtccaccaa | gacactcaag | gtggtggtgg | cagtggtggc | cagtttctt | 780 |
| atcttctggt | tgccctacca | ggtgacgggg | ataatgatgt | ccttcctgga | gccatcgtca | 840 |
| cccaccttcc | tgctgctgaa | taagctggac | tccctgtgtg | tctcctttgc | ctacatcaac | 900 |
| tgctgcatca | accccatcat | ctacgtggtg | gccggccagg | gcttccaggg | ccgactgcgg | 960 |
| aaatccctcc | ccagcctcct | ccggaacgtg | ttgactgaag | agtccgtggt | tagggagagc | 1020 |
| aagtcattca | cgcgctccac | agtggacact | atgcccagag | agacccaggc | agtgtaggcg | 1080 |
| acagcctcat | gggccactgt | ggcccgatgt | ccccttcctt | cccggccatt | ctccctcttg | 1140 |
| ttttcacttc | acttttcgtg | ggatggtgtt | accttagcta | actaactctc | ctccatgttg | 1200 |
| cctgtctttc | ccagacttgt | ccctcctttt | ccagcgggac | tcttctcatc | cttcctcatt | 1260 |
| tgcaaggtga | acacttcctt | ctagggagca | ccctcccacc | ccccaccccc | cccacacac | 1320 |
| catctttcca | tcccaggctt | ttgaaaaaca | aacagaaacc | cgtgtatctg | ggatatttcc | 1380 |
| atatggcaat | aggtgtgaac | agggaactca | gaatacagac | aagtagaaag | attctcgctt | 1440 |
| aaaaaaatgt | atttatttta | tggcaagttg | gaaaatatgt | aactggaatc | tcaaaagttc | 1500 |
| tttgggacaa | aacagaagtc | catggagtta | tctaagctct | tgtaagtgag | ttaatttaaa | 1560 |
| aaagaaaatt | aggctgagag | cagtggctca | cgcctgtaat | cccagaactt | tgggaggcta | 1620 |
| aggtgggtgg | atcacctgag | gtcaagagtt | ccagaccagg | ctggccagca | tggtgaaacc | 1680 |
| ccgtctgtac | taaaaataca | aaaattaac | tgggcatggt | agtgggtgcc | tgtaatccca | 1740 |
| gctacttggg | aggctgaggt | gggagaattg | ctcgaacctt | ggaggtggag | gttgtggtga | 1800 |
| gccatgatcg | caccactgca | ctctagcctg | ggtgaccgag | ggaggctctg | tctcaaaagc | 1860 |
| aaagcaaaaa | caaaaacaaa | aacacctaaa | aaacctgcag | ttttgtttgt | actttgttt | 1920 |
| taaattatgc | tttctatttt | gagatcattg | caaactcaac | acaattgtaa | gtaatgatac | 1980 |
| agagggatct | tgtgtacccct | tcacccagcc | tccccaatg | gcaacatctt | gcaaaactac | 2040 |
| aatgtagtct | cataaccagg | atattgacat | tgatacagtg | aagatacagg | acattctcat | 2100 |
| caccacaggg | atccccagga | tgcccacttc | cctccacccc | cacaccccag | ccgtgtccct | 2160 |

```
aacccctggc aaccaggaat ccactctcca tttctataat gttgtcattt caagaatgtt    2220
attcaatgga atcatatagt atgtaacctg ttttgagctt aaaaaaaaaa gtatacatga    2280
ctttaatgag gaaataaaa atgaatattg aaaaaaaaaa ctttagag                  2328
```

<210> SEQ ID NO 3
<211> LENGTH: 350
<212> TYPE: PRT
<213> ORGANISM: Homo sapiens

<400> SEQUENCE: 3

```
Met Asp Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30

Leu Arg Val Pro Asp Ile Leu Ala Leu Val Ile Phe Ala Val Val Phe
        35                  40                  45

Leu Val Gly Val Leu Gly Asn Ala Leu Val Val Trp Val Thr Ala Phe
    50                  55                  60

Glu Ala Lys Arg Thr Ile Asn Ala Ile Trp Phe Leu Asn Leu Ala Val
65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
            100                 105                 110

Pro Ser Leu Ile Leu Leu Asn Met Tyr Ala Ser Ile Leu Leu Leu Ala
        115                 120                 125

Thr Ile Ser Ala Asp Arg Phe Leu Leu Val Phe Lys Pro Ile Trp Cys
    130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
            180                 185                 190

Ser His Asp Lys Arg Arg Glu Arg Ala Val Ala Ile Val Arg Leu Val
        195                 200                 205

Leu Gly Phe Leu Trp Pro Leu Leu Thr Leu Thr Ile Cys Tyr Thr Phe
    210                 215                 220

Ile Leu Leu Arg Thr Trp Ser Arg Arg Ala Thr Arg Ser Thr Lys Thr
225                 230                 235                 240

Leu Lys Val Val Ala Val Val Ala Ser Phe Phe Ile Phe Trp Leu
                245                 250                 255

Pro Tyr Gln Val Thr Gly Ile Met Met Ser Phe Leu Glu Pro Ser Ser
            260                 265                 270

Pro Thr Phe Leu Leu Leu Asn Lys Leu Asp Ser Leu Cys Val Ser Phe
        275                 280                 285

Ala Tyr Ile Asn Cys Cys Ile Asn Pro Ile Ile Tyr Val Val Ala Gly
    290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
                325                 330                 335

Arg Ser Thr Val Asp Thr Met Ala Gln Lys Thr Gln Ala Val
            340                 345                 350
```

```
<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tggactacag ccacgacaaa cg                                              22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
aggaaggaca tcattatccc cg                                              22

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
caccagcccc gagatttttt c                                               21

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
tcagaaacca gatggcgt                                                   18
```

TRANSGENIC MOUSE COMPRISING A POLYNUCLEOTIDE ENCODING HUMAN OR HUMANIZED C5AR AND METHODS OF PRODUCTION AND USE

FIELD OF THE INVENTION

The present invention relates to transgenic non-human mammals comprising a polynucleotide encoding a human or humanized C5aR. The invention also relates to use of the transgenic non-human mammals in methods of screening for agonists, inverse agonists and antagonists of human C5aR and for testing efficacy of C5aR agonists, inverse agonists and antagonists in various animal models of disease.

BACKGROUND OF THE INVENTION

Proteolysis of each of the complement proteins C3-C5 gives rise to aminoterminal cationic fragments with signalling molecules called anaphylatoxins. The most potent of these, C5a, elicits the broadest responses. Considering the components of the inflammatory response as margination and infiltration of leukocytes, release of granule-bound proteolytic enzymes, production of activated oxygen and nitrogen-derived radicals, changes in blood flow and capillary leakage, along with the ability to contract smooth muscle, the C5a molecule is the "complete" pro-inflammatory mediator. At sub-nanomolar to nanomolar levels, the C5a molecule elicits chemotaxis of all myeloid lineages (neutrophils, eosinophils and basophils, macrophages and monocytes), and causes vascular permeability which is markedly potentiated by prostaglandins and circulating leukocytes. Higher nanomolar concentrations elicit degranulation and activation of NADPH oxidase. This breadth of bioactivity contrasts with other inflammatory mediators. C5a has been implicated in the pathogenesis of rheumatoid arthritis, psoriasis, sepsis, reperfusion injury, and adult respiratory distress syndrome.

The activities of C5a are mediated by the binding of the C5a to its receptor (C5aR). C5aR belongs to the family of seven transmembrane G-protein-coupled receptors. C5aR is a high affinity receptor for C5a, with a Kd of ~1 nM, and is located on a number of different cell types including leukocytes. The number of receptors per cell is extremely high, up to 200,000 sites per leukocyte. Biological activation of the receptor occurs over the range that saturates binding.

C5aR comprises an extended N-terminal extracellular domain. This large N-terminal domain is typical of G-protein coupled receptors which bind peptides including the IL-8 and fMet-Leu-Phe (FMLP) receptor families. The C5aR structure conforms to the seven transmembrane receptor family, with the extracellular N-terminus being followed by seven transmembrane helices connected by interhelical domains alternating as intracellular and extracellular loops, and ending with an intracellular C-terminal domain.

Agonists of C5aR are useful for therapeutic purposes, for example, in defence against bacterial infection, to stimulate immunoregulatory effects of C5a, and to treat cancers, immunodeficiency diseases and severe infections.

Antagonists of C5aR are also useful therapeutic agents, for example for treating inflammatory diseases and autoimmune disorders. For example, antagonists of C5aR are useful in the treatment of asthma, bronchial allergy, chronic inflammation, systemic lupus erythematosis, vasculitis, rheumatoid arthritis, osteoarthritis, gout, some auto-allergic diseases, transplant rejection, inflammatory bowel disease (for example, ulcerative colitis), in certain shock states, myocardial infarction, and post-viral encephalopathies. To this end, C5aR peptide antagonists and anti-C5a receptor antibodies have been previously described. For example, WO95/00164 describes antibodies directed against an N-terminal peptide (residues 9-29) of the C5a receptor.

Currently, alternative and/or improved C5aR antagonists and antagonists are desirable, as are improved methods of screening for C5aR antagonists and antagonists.

In vitro screening methods for detecting of C5aR agonists/antagonists are known in the art. For example, chemotaxis assays can be used to assess the ability of an antibody or functional fragment thereof to block binding of a ligand to C5aR and/or inhibit function associated with binding of the ligand to the receptor. These assays are based on the functional migration of cells in vitro induced by a compound. Chemotaxis can be assessed by any suitable means, such as in an assay utilizing a 96-well chemotaxis plate, or using other art-recognized methods for assessing chemotaxis. For example, the use of an in vitro transendothelial chemotaxis assay is described by Springer et al. (Springer et al., WO 94/20142, published Sep. 15, 1994; see also Berman et al., Immunol. Invest. 17: 625-677 (1988)). Migration across endothelium into collagen gels has also been described (Kavanaugh et al., J. Immunol., 146: 4149-4156 (1991)).

A critical requirement in the drug discovery process is the demonstration in relevant animal models that new therapeutic agents identified by in vitro screening methods are safe and effective. Moreover, it is often desirable to compare the in vivo efficacy of numerous agents to select for desirable properties including pharmacokinetic properties, efficacy in affecting disease outcome and lack of adverse side effects. One of the main obstacles to drug development is moving drug candidates from in vitro assays to demonstration of in vivo efficacy. Often this is because many drug candidates are species-specific. For instance, an antagonist developed to a human chemoattractant receptor, such as C5aR, might antagonise only human C5aR and not C5aR from mouse, rabbit or even higher primates. The inability of many drugs candidates to "work" across species is a major reason for attrition in the preclinical phase.

Improved screening methods that allow identification and/or testing of human C5aR agonists, inverse agonists and antagonists in an in vivo environment are therefore desirable.

SUMMARY OF THE INVENTION

The present inventors have found that a number of C5aR antagonists react with human C5aR but not C5aR from other species. For example, monoclonal antibodies MAb 7F3, MAb 6C12 and MAb 12D4 (described in PCT/AU03/00084) bind to human C5aR but do not bind to mouse or baboon C5aR. This brings to light the need for an in vivo screening and validation system that is capable of detecting and/or validating agonists/antagonists that are specific for human C5aR.

The present inventors have also found that chemotaxis of murine cells engineered to express human C5aR is inhibited by anti-human C5aR antibodies. This finding, coupled with the knowledge that murine C5a binds to human C5aR with high affinity, indicates that human C5aR is compatible with C5aR signalling machinery in other mammalian systems. The present inventors have therefore developed a transgenic non-human mammal that expresses a human C5aR and is useful for screening or testing of agonists/antagonists of C5aR, particularly those agonists/antagonists specific for human C5aR.

Accordingly, the present invention provides a transgenic non-human mammal comprising a polynucleotide encoding a human C5aR or humanized C5aR.

In one embodiment, the polynucleotide encodes human C5aR. Preferably, the polynucleotide encodes a polypeptide comprising a sequence as shown in SEQ ID NO:3, or an allelic variant thereof.

In a further embodiment, the polynucleotide comprises a sequence as shown in SEQ ID NO:2, or an allelic variant thereof.

In a further embodiment, the polynucleotide encodes humanized C5aR. By "humanized C5aR" we mean a non-human C5aR that has been modified so as to introduce or enhance at least one functional characteristic of native human C5aR. Preferably, the non-human C5aR is the C5aR endogenous to the transgenic mammal.

For example, the modification may alter the binding specificity of the non-human C5aR such that the humanized C5aR binds to one or more ligands, agonists, inverse agonists or antagonists of human C5aR. Alternatively, the modification may enhance the binding affinity of the non-human C5aR to one or more ligands, agonists, inverse agonists or antagonists of human C5aR. In one preferred embodiment, the modification enhances the binding affinity of the non-human C5aR to one or more ligands, agonists, inverse agonists or antagonists of human C5aR by at least 5 fold, more preferably by at least 10 fold.

The modification preferably involves substitution of at least one amino acid of the non-human C5aR with the corresponding amino acid of human C5aR.

Preferably, the modification comprises replacing at least one domain or a substantial part thereof with the corresponding domain of human C5aR or a substantial part thereof. For example, the modification may comprise replacing least one extracellular domain of the endogenous C5aR with the corresponding human C5aR extracellular domain. The humanized C5aR may thus comprises at least one extracellular domain of human C5aR. In one example, the humanized C5aR comprises intracellular domains of the endogenous C5aR and extracellular domains of human C5aR.

In a preferred embodiment the transgenic mammal has somatic and germline cells which contain, in a stably integrated form, a polynucleotide encoding human or humanized C5aR. In other words, it is preferred that the transgenic mammal is a "knock in" for human or humanized C5aR. It will be appreciated that this can be achieved by, for example, introducing a polynucleotide construct encoding human C5aR or a polynucleotide construct encoding humanized C5aR into the genome of a mammal by targeted integration into the genome of the mammal.

Alternatively, a polynucleotide construct encoding a fragment of human C5aR may be integrated within the endogenous C5aR sequence, such that following integration, the endogenous C5aR site comprises polynucleotide encoding humanized C5aR.

In a further preferred embodiment, the transgenic mammal is homozygous for human or humanized C5aR.

In a further preferred embodiment, expression of endogenous C5aR in the transgenic animal is undetectable or insignificant. Reduction in expression of endogenous C5aR may be achieved by any suitable means. For example, the cells of the transgenic mammal may be modified so as to express an antisense nucleic acid complementary to nucleic acids encoding endogenous C5aR. Alternatively, the endogenous C5aR gene may be disrupted by homologous recombination. Preferably, the transgenic mammal is a homozygous "knock out" for endogenous C5aR.

In a preferred embodiment of the invention, the "knock out" of endogenous C5aR occurs simultaneously with the introduction of human or humanized C5aR. This is preferably achieved by replacing the endogenous C5aR coding sequence or a fragment thereof with a corresponding human C5aR coding sequence or fragment thereof by way of targeted homologous recombination. In one particular embodiment of the invention, one or more of the domains of the endogenous C5aR is replaced with the corresponding human domain(s).

The transgenic animals of the present invention may comprise other genetic alterations in addition to the presence of a human C5aR encoding sequence. For example, the genome of the transgenic animal may be altered to affect the function of endogenous genes, contain marker genes, or other genetic alterations consistent with the methods of the present invention.

In a further preferred embodiment of the invention, the transgenic non-human mammal is selected from the group consisting of a cow, pig, goat, sheep, camel, horse, cat, dog, monkey, baboon, rabbit, guinea pig, rat, hamster and mouse. Rodents such as rats, mice and hamsters are preferred mammals. Preferably, the transgenic mammal is a mouse.

The present invention also provides an isolated tissue, isolated organ, isolated cell(s), primary cell culture or established cell line obtained from the transgenic non-human mammal of the invention. Preferred organs or tissues include smooth muscle, endothelial tissue, contractile muscle and heart.

The present invention also provides a method for producing a transgenic non-human mammal, the method comprising introducing into the genome of a non-human mammal a polynucleotide construct encoding human C5aR, humanized C5aR or a fragment of human C5aR, to produce a transgenic non-human mammal.

In one embodiment, the polynucleotide construct encodes human C5aR. Preferably, the polynucleotide encodes a polypeptide comprising a sequence as shown in SEQ ID NO:3, or an allelic variant thereof.

In a further embodiment, the polynucleotide construct comprises a sequence as shown in SEQ ID NO:2, or an allelic variant thereof.

In a further embodiment, the polynucleotide construct encodes humanized C5aR.

In a further embodiment of the invention, the polynucleotide construct encodes a fragment of human C5aR. Preferably, the fragment encompasses at least one domain of human C5aR or a part thereof.

In a preferred embodiment of the invention, the fragment encompasses at least one of the domains listed in Table 1. In one particular embodiment, the fragment encompasses at least one extracellular domain of human C5aR. In another embodiment, the fragment encompasses two or more of the domains listed in Table 1.

In a further preferred embodiment, the method further comprises disrupting the endogenous C5aR of the non-human mammal. Preferably, the transgenic mammal is a homozygous "knock out" for endogenous C5aR.

In a preferred embodiment the method comprises replacing the endogenous C5aR coding sequence or a fragment thereof with a corresponding human C5aR coding sequence or fragment thereof by way of targeted homologous recombination. In one particular embodiment of the invention, the method comprises replacing one or more of the domains of the endogenous C5aR with the corresponding human domain(s).

In a further preferred embodiment the polynucleotide construct comprises a selectable marker. Any suitable selectable marker may be used, although a preferred selectable marker is the PGK-neo gene. Preferably, the selectable marker is flanked by loxP sites so that the selectable marker can be removed after targeting by transient expression of the Cre recombinase.

In a further preferred embodiment, the polynucleotide construct comprises regions homologous to the 3' and 5' sequences flanking the endogenous C5aR coding sequence of the non-human mammal. Preferably, the polynucleotide construct comprises regions homologous to at least 2 kb, more preferably around 3 kb, upstream and downstream of exon 3 of the endogenous C5aR gene.

It will be appreciated that the transgenic mammals of the present invention will be useful in the identification, evaluation or validation of novel agonists, inverse agonists and antagonists of C5aR. For example, transgenic mammals of the present invention can be used to screen a number of candidate compounds to identify agonists, inverse agonists or antagonists of human C5aR function. The transgenic mammals of the present invention can also be used to evaluate the therapeutic suitability of agonists, inverse agonists or antagonists of human C5aR function that have previously been identified in screening methods.

Accordingly, the present invention also provides a method for evaluating at least one pharmacokinetic and/or pharmacodynamic effect of a candidate compound, the method comprising administering a candidate compound to a transgenic mammal of the present invention or isolated tissue or cells obtained therefrom and examining at least one pharmacokinetic and/or pharmacodynamic effect of the candidate compound on the transgenic mammal.

In a preferred embodiment, the at least one pharmacokinetic effect examined is an absorption parameter, a distribution parameter, a metabolism parameter, or an excretion parameter.

For example, the at least one pharmacokinetic effect examined may be volume of distribution, total clearance, protein binding, tissue binding, metabolic clearance, renal clearance, hepatic clearance, biliary clearance, intestinal absorption, bioavailability, relative bioavailability, intrinsic clearance, mean residence time, maximum rate of metabolism, Michaelis-Menten constant, partitioning coefficients between tissues and blood or plasma, fraction excreted unchanged in urine, fraction of drug systemically converted to metabolites, elimination rate constant, half-life, or secretion clearance.

For purposes of clarity and to assist in understanding the full scope of the present invention, "pharmacokinetic effects" refers to the study of the kinetics associated with the dynamic processes of a parameter such as absorption, distribution, metabolism, and excretion (ADME) of a candidate compound and/or its metabolites within a living organism. As used within the context of the present invention, the following pharmacokinetic terms shall be construed broadly, and shall have their generally accepted meanings as set forth below.

"Absorption" refers to the process of uptake of a candidate compound from the site of administration into the systemic circulation. The transfer of the candidate compound across the intestinal lumen is generally referred to as oral absorption, whereas the transfer of the candidate compound across an external physiological barrier is referred to general absorption. The pharmacokinetic parameter of absorption may be estimated from biosensor data associated with a sensor chip having, for example, a plurality of appropriate liposomes immobilized thereon.

"Distribution" refers to the transfer of a candidate compound from the site of administration to the total systemic circulation and then to extracellular and intracellular water and tissues. Distribution is usually a rapid and reversible process. The pharmacokinetic parameter of distribution may be estimated from biosensor data associated with a sensor chip having, for example, a plurality of appropriate plasma proteins, liposomes, and/or transport proteins immobilized thereon.

"Metabolism" refers to the sum of all the chemical reactions for biotransformation of endogenous and exogenous substances which take place in the living cell. The pharmacokinetic parameter of metabolism may be estimated from biosensor data associated with a sensor chip having, for example, a plurality of appropriate metabolic enzymes immobilized thereon.

"Excretion" refers to the final elimination or loss of a drug from the body. Excretion includes both passive diffusion and relative specific carrier mediated excretion. Candidate compounds may be excreted, unchanged or as metabolites, in urine via the kidneys or in feces via the bile and/or the intestine. Volatile compounds are often excreted in expired air by the lungs. The pharmacokinetic parameter of excretion may be estimated from biosensor data associated with a sensor chip having immobilized thereon, for example, an antibody that specifically detects the candidate compound, as well as other proteins/receptors having a high affinity/specificity against the drug candidate. Such antibodies and proteins/receptors may be used to quantify the concentration/amount of the drug in different body fluids (e.g., urine/feces) and tissues, using a direct binding assay.

In another embodiment, the method involves examining at least one pharmacodynamic effect of the candidate compound on the transgenic mammal. Preferably, the at least one pharmacodynamic effect is modulation of C5aR activity. This can be assessed by monitoring at least one phenotype associated with C5aR signalling following administration of the candidate compound.

Accordingly, in another embodiment the present invention provides a method of identifying a compound that modulates C5aR activity, the method comprising (i) administering a candidate compound to a transgenic mammal of the present invention or isolated tissue or cells obtained therefrom under conditions in which at least one phenotype associated with C5aR signalling is expressed; and (ii) monitoring development of the at least one phenotype following administration of the compound.

In a preferred embodiment the method further comprises (iii) comparing the extent of the phenotype in the transgenic mammal or cells derived therefrom to which the compound was administered relative to a control mammal or cells derived therefrom, wherein any difference in the nature or extent of the phenotype when compared to the control mammal indicates the potential of the compound to modulate C5aR activity.

In one particular embodiment the present invention provides a method of identifying a compound that inhibits or reduces C5aR activity, the method comprising (i) administering a candidate compound to a transgenic mammal of the present invention or isolated tissue or cells obtained therefrom under conditions in which at least one phenotype associated with C5aR signalling is expressed; and (ii) monitoring development of the at least one phenotype following administration of the compound, wherein any reduction or inhibition in the nature or extent of the phenotype following administration indicates the potential of the compound to inhibit or reduce C5aR activity. Preferably, the method further comprises (iii) comparing the extent of the phenotype in the transgenic mammal to which the compound was administered relative to a control mammal, wherein any reduction or inhibition in the nature or extent of the phenotype when compared to the control mammal indicates the potential of the compound to inhibit or reduce C5aR activity.

In another embodiment the present invention provides a method of identifying a compound that promotes or enhances C5aR activity, the method comprising (i) administering a candidate compound to a transgenic mammal of the present invention or isolated tissue or cells obtained therefrom under conditions in which at least one phenotype associated with C5aR signalling is expressed; and (ii) monitoring development of the at least one phenotype following administration of the compound, wherein any enhancement in the nature or extent of the phenotype following administration indicates the potential of the compound to promote or enhance C5aR activity. Preferably, the method further comprises (iii) comparing the extent of the phenotype in the transgenic mammal to which the compound was administered relative to a control mammal, wherein any enhancement in the nature or extent of the phenotype when compared to the control mammal indicates the potential of the compound to promote or enhance C5aR activity.

The "control" animal employed in this context can be any other mammal that expresses the same phenotypic indictors as those expressed in the mammal on which the compound was tested (i.e. the "test" mammal).

In one embodiment, the control and test animals express similar levels of functional human C5aR. For example, the control and test animals may be isogenic.

In another embodiment, the control animal is a wild type animal that does not express human or humanized C5aR.

The phrase "phenotype associated with C5aR signalling" is intended to encompass any visible characteristic and/or behaviour (including a clinical symptom of a disease) that is associated with a biochemical process involving C5aR signalling. The phenotype may be associated with normal or aberrant C5aR signalling. In one embodiment the phenotype is a condition that is aggravated by C5aR signalling such as an immune complex disorder, an inflammatory or allergic disease, graft rejection or cancer. In another embodiment, the phenotype is a condition that is alleviated or abated by increased C5aR signalling such as a condition associated with immunosuppression.

In one particular embodiment, the phenotype is inflammation. The inflammation may be induced, for example, by transfer of serum from an arthritic K/BxN mammal into a transgenic mammal of the invention.

In another embodiment the phenotype is inflammatory tissue damage such as ischaemia-reperfusion injury.

In another embodiment, the phenotype is leukocyte infiltration.

In another embodiment, the phenotype is asthma.

In another embodiment, the phenotype is sepsis, stroke or respiratory distress syndrome.

In another embodiment, the phenotype is a condition selected from the group consisting of inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, anlcylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease; graft rejection (e.g., in transplantation), including allograft rejection or graft-versus-host disease; atherosclerosis; cancers with leukocyte infiltration of the skin or organs; reperfusion injury, stroke, adult respiratory distress syndrome, certain hematologic malignancies, cytokine-induced toxicity (e.g., septic shock, endotoxic shock), polymyositis, dermatomyositis, pemphigoid, Alzheimers Disease, granulomatous diseases including sarcoidosis, immunodeficiency syndromes such as AIDS, radiation therapy, chemotherapy, therapy for autoimmune disease or other drug therapy (e.g., corticosteroid therapy), which causes immunosuppression; and immunosuppression due congenital deficiency or infectious diseases such as Severe Acute Respiratory Syndrome (SARS).

The range of candidate compounds contemplated herein include C5aR inhibitory compounds or inverse agonists or antagonists of a biological function of C5aR. In one embodiment, the compound is selected from the group consisting of: a peptide, including a peptide derived from C5aR or C5a or other non-C5aR peptides and capable of inhibiting, reducing or repressing a C5aR function, a C5aR dominant-negative mutant; a non peptide inhibitor of C5aR; an antibody or antibody fragment which binds to C5aR and inhibits a C5aR function; a small organic molecule, and nucleic acid, including nucleic acid encoding said peptide derived from C5aR or C5a or other non-C5aR peptide inhibitor, an antisense nucleic acid directed against C5aR-encoding mRNA, or an anti-C5aR ribozyme, or a small interfering RNA (RNAi) that targets C5aR gene expression.

The present invention also provides a method of identifying a compound that modulates C5aR activity, the method comprising (a) administering a candidate compound to a transgenic mammal of the present invention or isolated tissue or cells obtained therefrom under conditions in which at least one phenotype associated with C5aR signalling is expressed; and monitoring development of the at least one phenotype following administration of the compound (b) optionally, determining the structure of the candidate compound; and (c) providing the candidate compound or the name or structure of the candidate compound.

Naturally, for agents that are known albeit not previously tested for their function using a screen provided by the present invention, determination of the structure of the compound is implicit in step (b). This is because the skilled artisan will be aware of the name and/or structure of the compound at the time of performing the screen.

As used herein, the term "providing the agent" shall be taken to include any chemical or recombinant synthetic means for producing said agent or alternatively, the provision of an agent that has been previously synthesized by any person or means.

In embodiment of the present invention, the subject method further comprises formulating the identified compound for administration to a non-human animal or a human. The formulations can be suitable for administration by injection by a subcutaneous, intravenous, intranasal, or intraperitoneal route. Alternatively, they can be suitable for oral administration in the form of feed additives, tablets, troches, etc.

In another aspect, the present invention provides a compound identified by a method of the present invention.

The various features and embodiments of the present invention, referred to in individual sections above apply, as appropriate, to other sections, mutatis mutandis. Consequently features specified in one section may be combined with features specified in other sections, as appropriate.

KEY TO SEQUENCE LISTINGS

Figure 1:
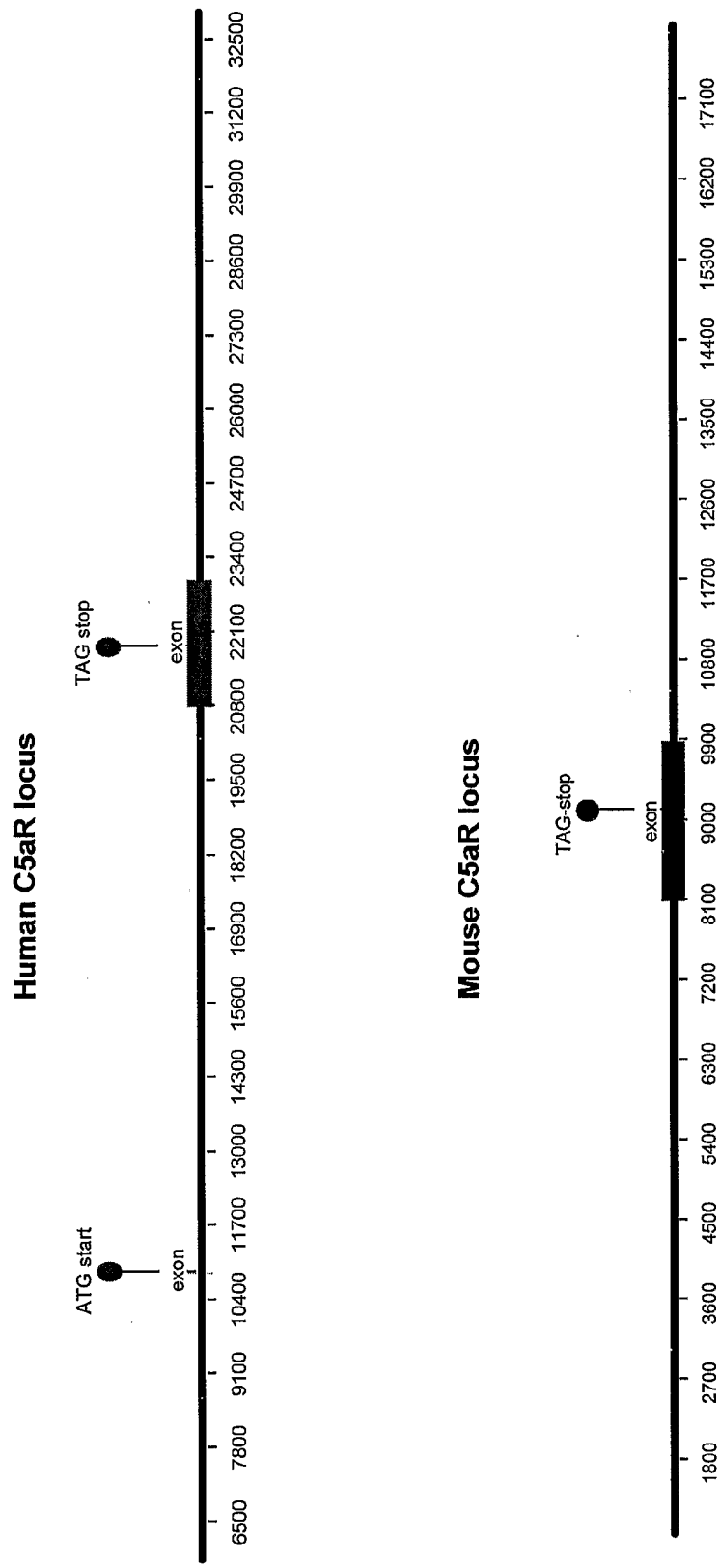
FIG. 1: Diagram showing design of targeting construct for generation of human C5aR knock-in mice.
Figure 1:
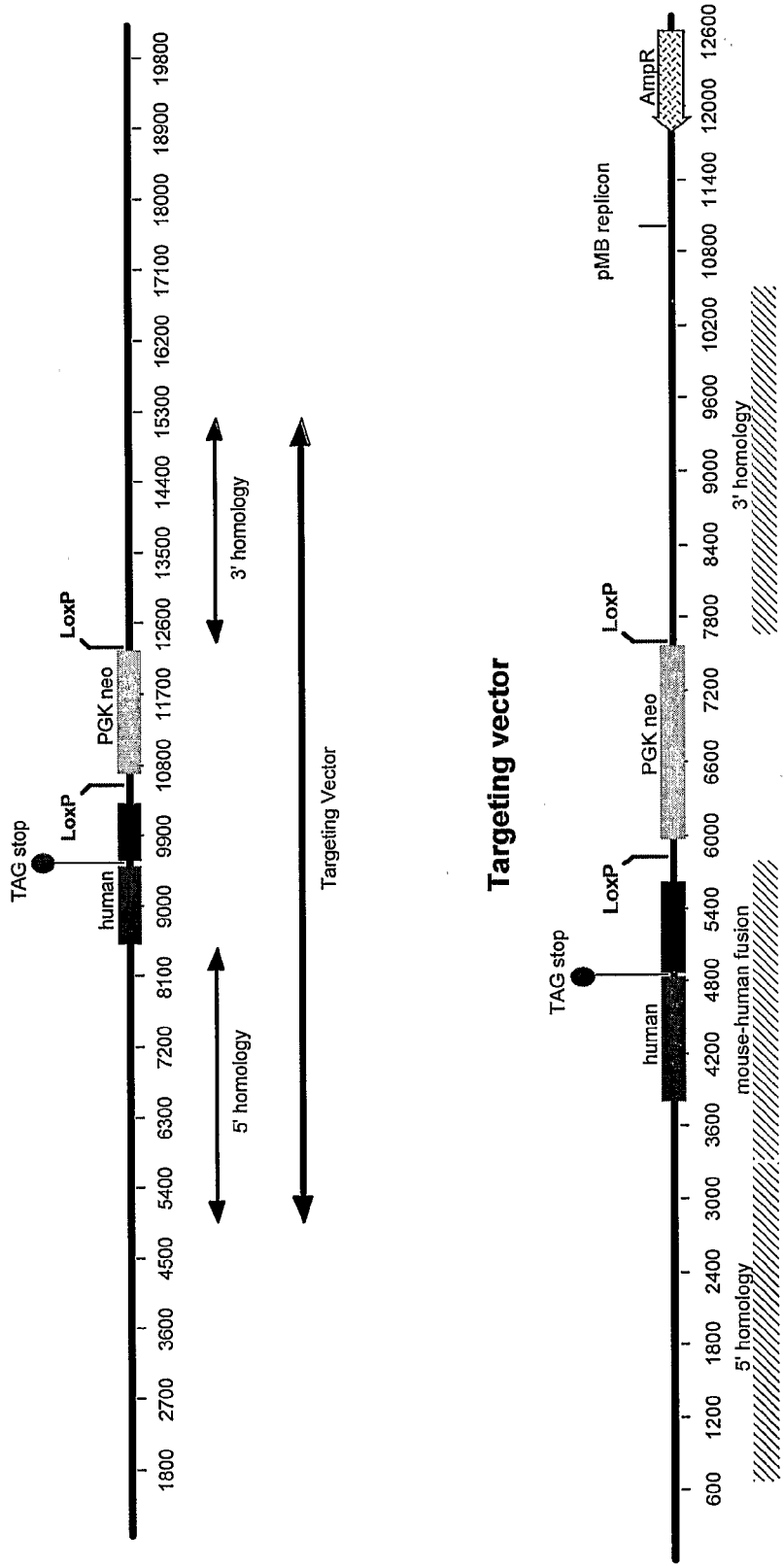

SEQ ID NO:1: Sequence of mouse C5aR(C5r1) gene locus and flanking DNA.
SEQ ID NO:2: Sequence of human C5aR cDNA.
SEQ ID NO:3: Amino acid sequence of human C5aR.
SEQ ID NO:4: Primer F1C (specific for human C5aR exon 3):
SEQ ID NO:5: Primer R2a (specific for human C5aR exon 3):
SEQ ID NO:6: Primer F3C (specific for the mouse C5aR gene):
SEQ ID NO:7: Primer R4C (specific for the mouse C5aR gene):

DETAILED DESCRIPTION OF THE INVENTION

General Techniques and Definitions

Unless otherwise indicated, the recombinant DNA techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al, Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al (Editors), Current Protocols in Molecular Biology, Greene Pub. Associates and Wiley-Interscience (1988, including all updates until present) and are incorporated herein by reference. In particular, these documents describe in detail methods of transcribing or replicating nucleic acid molecules and suitable conditions required therefor.

Definitions

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, a "ligand" of a C5aR protein refers to a particular class of substances which bind to a mammalian C5aR protein, including natural ligands and synthetic and/or recombinant forms of natural ligands. In a preferred embodiment, ligand binding of a C5aR protein occurs with high affinity.

As used herein, an "antagonist" is a substance which inhibits the binding of an agonist or inverse agonist to a C5aR protein and thus prevents at least one function characteristic of a C5aR protein such as a binding activity (e.g., ligand binding, promoter binding, antibody binding), a signaling activity (e.g., activation of a mammalian G protein, induction of rapid and transient increase in the concentration of cytosolic free calcium) and/or cellular response function (e.g., stimulation of chemotaxis, exocytosis or inflammatory mediator release by leukocytes). The term antagonist encompasses substances which bind receptor (e.g., an antibody, a mutant of a natural ligand, small molecular weight organic molecules, other competitive inhibitors of ligand binding), and substances which block receptor function without binding thereto.

As used herein, an "agonist" is a substance which promotes (induces, causes, enhances or increases) at least one function characteristic of a C5aR protein such as a binding activity (e.g., ligand, inhibitor and/or promoter binding), a signaling activity (e.g., activation of a mammalian G protein, induction of rapid and transient increase in the concentration of cytosolic free calcium) and/or a cellular response function (e.g., stimulation of chemotaxis, exocytosis or inflammatory mediator release by leukocytes). The term agonist encompasses substances which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

"Inverse agonist" as used herein refers to a molecule that binds to or otherwise interacts with the C5aR to inhibit the baseline intracellular response initiated by the active form of C5aR below the normal base level of activity which is observed in the absence of agonists By "transgenic mammal" is meant a mammal (e.g., mouse, rat, hamster, etc.), having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

The term "biologically active" or "functional", when used herein as a modifier of human C5aR, refers to a polypeptide that exhibits at least one of the functional characteristics attributed to native human C5aR, such as the ability to function as a C5a receptor or to bind to one or more natural ligands of human C5aR.

A "knock-out" of a gene means an alteration in the sequence of the gene that results in a decrease of function of the target gene, preferably such that target gene expression is undetectable or insignificant. A knock-out of an endogenous gene means that function of the gene has been substantially decreased so that expression is not detectable or only present at insignificant levels. "Knock-out" transgenics can be transgenic animals having a heterozygous knock-out of a gene or a homozygous knock-out of a gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic)) of the target gene, e.g., by introduction of an additional copy of the target gene, or by operatively inserting a regulatory sequence that provides for enhanced expression of an endogenous copy of the target gene. "Knock-in" transgenics of interest for the present invention are transgenic animals having a knock-in of a human or humanized C5aR. Such transgenics can be heterozygous knock-in for the human or humanized C5aR gene or homozygous for the knock-in of the human or humanized C5aR gene. "Knock-ins" also encompass conditional knock-ins.

By "construct" is meant a recombinant nucleic acid, generally recombinant DNA, that has been generated for the purpose of the expression of a specific nucleotide sequence, or is to be used in the construction of other recombinant nucleotide sequences.

By "operably linked" is meant that a DNA sequence and a regulatory sequence are connected in such a way as to permit gene expression when the appropriate molecules (e.g., transcriptional activator proteins) are bound to the regulatory sequence.

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by a human C5aR sequence).

The term "corresponds to" or "corresponding to" is meant homologous to or substantially equivalent to or functionally equivalent to the designated sequence.

The term "transgenic gene construct" refers to a nucleic acid molecule, e.g., a vector, containing the subject polynucleotide, e.g., the human C5aR polynucleotide or fragment thereof, operably linked in a manner capable of expressing the polynucleotide in a host cell. As used herein, the term "polynucleotide" encompasses deoxyribonucleic acid (DNA), and, where appropriate, ribonucleic acid (RNA). As used herein the term also encompasses analogs of either RNA or DNA made from nucleotide analogs, and, as applicable to the embodiment being described, single-stranded (such as sense or antisense) and double-stranded polynucleotides.

Transgenic Animals

Techniques for producing transgenic animals are well known in the art. A useful general textbook on this subject is Houdebine, Transgenic animals—Generation and Use (Harwood Academic, 1997)—an extensive review of the techniques used to generate transgenic animals from fish to mice and cows. Of particular interest in the context of the present invention are transgenic non-human mammals such as cows, pigs, goats, horses, etc., and particularly rodents, e.g. rats, mice, hamsters, etc. Preferably, the transgenic animal is a mouse.

Advances in technologies for embryo micromanipulation now permit introduction of heterologous DNA into, for example, fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are transfected with the desired DNA by electroporation, and transgenic animals produced from the infected embryo. In a further preferred method, however, the appropriate DNAs are coinjected into the pronucleus or cytoplasm of embryos, preferably at the single cell stage, and the embryos allowed to develop into mature transgenic animals. Those techniques as well known. See reviews of standard laboratory procedures for microinjection of heterologous DNAs into mammalian fertilized ova, including Hogan et al., Manipulating the Mouse Embryo, (Cold Spring Harbor Press 1986); Krimpenfort et al., Bio/Technology 9:844 (1991); Palmiter et al., Cell, 41: 343 (1985); Kraemer et al., Genetic manipulation of the Mammalian Embryo, (Cold Spring Harbor Laboratory Press 1985); Hammer et al., Nature, 315: 680 (1985); Wagner et al., U.S. Pat. No. 5,175,385; Krimpenfort et al., U.S. Pat. No. 5,175,384, the respective contents of which are incorporated herein by reference.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology as described in Schnieke, A. E. et al., 1997, Science, 278: 2130 and Cibelli, J. B. et al., 1998, Science, 280: 1256. Using this method, fibroblasts from donor animals are stably transfected with a plasmid incorporating the coding sequences for a binding domain or binding partner of interest under the control of regulatory. Stable transfectants are then fused to enucleated oocytes, cultured and transferred into female recipients.

Analysis of animals which may contain transgenic sequences would typically be performed by either PCR or Southern blot analysis following standard methods.

By way of a specific example for the construction of transgenic mammals, such as cows, nucleotide constructs comprising a sequence encoding a binding domain fused to GFP are microinjected using, for example, the technique described in U.S. Pat. No. 4,873,191, into oocytes which are obtained from ovaries freshly removed from the mammal. The oocytes are aspirated from the follicles and allowed to settle before fertilization with thawed frozen sperm capacitated with heparin and prefractionated by Percoll gradient to isolate the motile fraction.

The fertilized oocytes are centrifuged, for example, for eight minutes at 15,000 g to visualize the pronuclei for injection and then cultured from the zygote to morula or blastocyst stage in oviduct tissue-conditioned medium. This medium is prepared by using luminal tissues scraped from oviducts and diluted in culture medium. The zygotes must be placed in the culture medium within two hours following microinjection.

Oestrous is then synchronized in the intended recipient mammals, such as cattle, by administering coprostanol. Oestrous is produced within two days and the embryos are transferred to the recipients 5-7 days after estrous. Successful transfer can be evaluated in the offspring by Southern blot.

Alternatively, the desired constructs can be introduced into embryonic stem cells (ES cells) and the cells cultured to ensure modification by the transgene. The modified cells are then injected into the blastula embryonic stage and the blastulas replaced into pseudopregnant hosts. The resulting offspring are chimeric with respect to the ES and host cells, and nonchimeric strains which exclusively comprise the ES progeny can be obtained using conventional cross-breeding. This technique is described, for example, in WO91/10741.

Transgenic animals comprise an exogenous nucleic acid sequence present as an extrachromosomal element or stably integrated in all or a portion of its cells, especially in germ cells. It is preferred that a transgenic animal comprises stable changes to the germline sequence. A stable change is generally achieved by introduction of the DNA into the genome of the cell. Vectors for stable integration include plasmids, retroviruses and other animal viruses, YACs, and the like. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

In a preferred embodiment, the transgenic non-human mammals of the invention are produced by introducing a human C5aR transgene into the germline of the non-human animal. Embryonal stem cell (ES) are the primary type of target cell for introduction of the human C5aR transgene into the non-human animal in order to achieve homologous recombination. ES cells may be obtained from pre-implantation embryos cultured in vitro and fused with embryos (Evans, M. J., et al. (1981) Nature 292, 154-156; Bradley, M. O., et al. (1984) Nature 309, 255-258; Gossler, et al. (1986) Proc. Natl. Acad. Sci U.S.A. 83, 9065-9069; and Robertson, et al. (1986) Nature 322, 445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468-1474. The transfected embryonal cells may be incubated in vitro for varying amounts of time, or reimplanted into the surrogate host, or both.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, in transgenic mice, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis. Progeny of the transgenic animals may be obtained by mating the transgenic animal with a suitable partner, or by in vitro fertilization of eggs and/or sperm obtained from the transgenic animal.

Methods of producing transgenic mice via homologous recombination between the endogenous gene and a transgene construct are described by Hanks, M et al (Science 269: 679-682, 1995), which is specifically incorporated herein by reference.

Human and Humanized C5aR Constructs

The introduced polynucleotide construct may encode a wild-type human C5aR sequence as shown in SEQ ID NO:3, or an allelic variant, biologically active derivative or fragment thereof.

Non-limiting examples of an allelic variants of SEQ ID NO:3 comprise one or more of the following substitutions:
Amino acid no. 2: Asp>Asn
Amino acid no. 279: Asn>Lys.

The polynucleotide construct may comprise a sequence as shown in SEQ ID NO:2, or an allelic variant thereof.

Non-limiting examples of an allelic variants of SEQ ID NO:2 comprise one or more of the following base changes:
Base no. 28: g>a
Base no. 474: c>t
Base no. 861: t>g
Base no. 1313-1314: insertion of a
Base no. 1447-1448: insertion of a.

The phrase "biologically active derivative" in relation to the amino acid sequence of human C5aR includes any substitution of, variation of, modification of, replacement of, deletion of or addition of one (or more) amino acids from or to the sequence shown in SEQ ID NO:3 providing the resultant amino acid sequence has human C5aR activity, preferably having at least 25 to 50% of the activity as the polypeptides presented in SEQ ID NO:3, more preferably at least substantially the same activity. Preferably, the human C5aR includes regions sufficient to effect signalling by C5aR.

Thus, the human C5aR sequence shown in SEQ ID NO:3 may be modified for use in the present invention. Typically, modifications are made that maintain the native activity of the sequence. Thus, in one embodiment, amino acid substitutions may be made, for example from 1, 2 or 3 to 10, 20 or 30 substitutions provided that the modified sequence retains at least about 25 to 50% of, or substantially the same C5aR signalling. However, in an alternative embodiment, modifications to the amino acid sequences of SEQ ID NO:3 may be made intentionally to reduce the biological activity of the polypeptide.

In general, preferably less than 20%, 10% or 5% of the amino acid residues of a biologically active derivative are altered as compared with the corresponding region depicted in SEQ ID NO:3.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |

|   |   |   |
|---|---|---|
|   | Polar - charged | D E |
|   |   | K R |
| AROMATIC |   | H F W Y |

In a preferred embodiment of the invention, the C5aR coding sequence is operably linked to a promoter, which may be endogenous or heterologous, constitutive or inducible, and other regulatory sequences required for expression in the host animal.

Alternatively, the introduced construct may encode humanized C5aR. Preferably, the humanized C5aR sequence is a modified version of a non-human C5aR, more preferably it is a modified version of the C5aR sequence endogenous to the transgenic mammal. The modification introduces or enhances at least one functional characteristic of native human C5aR in the humanized C5aR when compared to the non-human or endogenous C5aR. For example, if the non-human C5aR does not bind to a particular ligand, agonist inverse agonists or antagonist of human C5aR, the modification may alter the binding specificity such that the resultant humanized C5aR binds to that ligand, agonist inverse agonists or antagonist. Alternatively, if the non-human C5aR exhibits a low binding affinity for a particular ligand, agonist inverse agonists or antagonist of human C5aR, the modification may result in a humanized C5aR that exhibits enhanced binding affinity for that ligand, agonist, inverse agonist or antagonist when compared to the non-human C5aR. In one preferred embodiment, the modification enhances the binding affinity of the humanized C5aR to one or more ligands, agonists, inverse agonists or antagonists of human C5aR by at least 5 fold, more preferably by at least 10 fold, more preferably at least 20 fold, more preferably at least 50 fold, more preferably at least 100 fold, when compared to the non-human sequence.

The modification preferably involves substitution of at least one amino acid of the non-human C5aR with the corresponding amino acid of human C5aR. More preferably, the modification involves substitution of at least two, more preferably at least 5, more preferably at least 10, more preferably at least 20 amino acids of the non-human C5aR with the corresponding amino acids of human C5aR.

Preferably, the modification comprises replacing at least one domain or a substantial part thereof in the non-human C5aR with the corresponding domain of human C5aR or a substantial part thereof. For example, the modification may comprise replacing least one extracellular domain of the endogenous C5aR with the corresponding human C5aR extracellular domain. The humanized C5aR may thus comprises at least one extracellular domain of human C5aR. In one example, the humanized C5aR comprises intracellular domains of the endogenous C5aR and extracellular domains of human C5aR.

The various domains of human C5aR that may be introduced into the humanized C5aR are listed in Table 1.

TABLE 1

| amino acids | 1-37 | extracellular domain - N-terminus |
|---|---|---|
| amino acids | 38-60 | transmembrane domain |
| amino acids | 61-71 | intracellular domain |
| amino acids | 72-94 | transmembrane domain |
| amino acids | 95-110 | extracellular domain - extracellular loop 1 |
| amino acids | 111-132 | transmembrane domain |
| amino acids | 133-153 | intracellular domain |
| amino acids | 154-174 | transmembrane domain |
| amino acids | 175-200 | extracellular domain - extracellular loop 2 |

TABLE 1-continued

| amino acids | 201-226 | transmembrane domain |
|---|---|---|
| amino acids | 227-242 | intracellular domain |
| amino acids | 243-265 | transmembrane domain |
| amino acids | 266-282 | extracellular domain - extracellular loop 3 |
| amino acids | 283-303 | transmembrane domain |
| amino acids | 304-350 | intracellular domain - C-terminus. |

Constructs for use in the present invention include any construct suitable for use in the generation of transgenic animals having the desired levels of expression of the human or humanized C5aR-encoding sequence. These constructs may contain cDNA, genomic sequences, or both. Methods for isolating and cloning a desired sequence, as well as suitable constructs for expression of a selected sequence in a host animal, are well known in the art. The construct can include sequences other than the C5aR-encoding sequences. For example, a marker gene such as lac Z may be included in the construct, where upregulation of expression of the encoded sequence will result in an easily detected change in phenotype.

The term "C5aR gene" is used generically to mean a human C5aR gene and isoforms, alternate forms, splice variants, mutated variants, etc. of this human gene. This term is also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequence encoding C5aR may be cDNA or genomic DNA or a fragment thereof. The gene may be introduced into an appropriate vector for extrachromosomal maintenance or for integration into the host.

The genomic sequences of particular interest comprise the nucleic acid present between the initiation codon and the stop codon, including all of the introns that are normally present in a native chromosome. They may further include the 3' and 5' untranslated regions found in the mature mRNA. They may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kb or smaller; and substantially free of flanking chromosomal sequence.

The sequences of the 5' regions of the human C5aR gene, and further 5' upstream sequences and 3' downstream sequences, may be utilized for promoter elements, including enhancer binding sites, that provide for expression in tissues where C5aR is normally expressed. The tissue specific expression is useful for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) Mol Med 1: 194-205; Mortlock et al. (1996) Genome Res. 6:327-33; and Joulin and Richard-Foy (1995) Eur J Biochem 232: 620-626.

In one embodiment, vectors suitable for use in the present invention may comprise at least one expression control element operably linked to the nucleic acid sequence encoding human C5aR. Expression control elements may be inserted in the vector to control and regulate the expression of the nucleic acid sequence. Examples of expression control elements include, but are not limited to, lac system, operator and promoter regions of phage lamda, yeast promoters, and promoters derived from polyoma, adenovirus, retroviruses, or SV40. The vector may further comprise additional operational elements including, but not limited to, leader sequences, termination codons, polyadenylation signals, and any other sequences necessary or preferred for the appropriate transcription and/or translation of the nucleic acid sequence encoding human C5aR.

In a further preferred embodiment, the construct comprises regions homologous to the 3' and 5' sequences flanking the endogenous C5aR coding sequence of the non-human mammal. It will be understood that these regions of homology useful for targeted integration of the construct into the endogenous C5aR locus of the transgenic mammal.

Preferably, the polynucleotide construct comprises regions homologous to at least 2 kb, more preferably around 3 kb, upstream and downstream of exon 3 of the endogenous C5aR gene. For example, the upstream and downstream sequences may be derived from the sequence between nucleotides 7377-15045 of SEQ ID NO:1.

It will be further understood by one skilled in the art that such vectors are constructed using conventional methodology (See e.g. Sambrook et al., (eds.) (1989) "Molecular Cloning, A Laboratory Manual" Cold Spring Harbor Press, Plainview, N.Y.; Ausubel et al., (eds.) (1987) "Current Protocols in Molecular Biology" John Wiley and Sons, New York, N.Y.) or are commercially available.

In some embodiments it may be preferable to express human C5aR in tissues that mimic the native pattern of expression in humans. A specific expression pattern may be accomplished by placing the nucleic acid encoding the human C5aR under the control of an inducible or developmentally regulated promoter, or under the control of a tissue specific or cell type specific promoter. By way of example, specific expression patterns may be accomplished by the use of genomic sequences for human C5aR.

Techniques for in vitro mutagenesis of cloned genes are known. Examples of protocols for scanning mutations may be found in Gustin et al., 1993 Biotechniques 14:22; Barany, 1985 Gene 37:111-23; Colicelli et al., 1985 Mol Gen Genet 199:537-9; and Prentki et al., 1984 Gene 29:303-13. Methods for site specific mutagenesis can be found in Sambrook et al., 1989 Molecular Cloning: A Laboratory Manual, CSH Press, pp. 15.3-15.108; Weiner et al., 1993 Gene 126:35-41; Sayers et al., 1992 Biotechniques 13:592-6; Jones and Winistorfer, 1992 Biotechniques 12:528-30; Barton et al., 1990 Nucleic Acids Res 18:7349-55; Marotti and Tomich, 1989 Gene Anal Tech 6:67-70; and Zhu 1989 Anal Biochem 177:120-4.

"Knock Outs" and "Knock Ins"

Although not necessary to the operability of the invention, the transgenic animals described herein may comprise alterations to endogenous genes in addition to the genetic alterations described above. For example, the host animals may be either "knockouts" and/or "knockins" for a target gene(s) as is consistent with the goals of the invention (e.g, the host animal's endogenous C5aR may be "knocked out" and/or a human C5aR "knocked in"). Knockouts have a partial or complete loss of function in one or both alleles of an endogenous gene of interest (e.g., C5aR). Knockins have an introduced transgene with altered genetic sequence and/or function from the endogenous gene. The two may be combined, for example, such that the naturally occurring gene is disabled, and an altered form introduced. For example, it is preferable to knockout the host animal's endogenous C5aR gene, while introducing an a human C5aR gene.

In a knockout, preferably the target gene expression is undetectable or insignificant. For example, a knock-out of a C5aR gene means that function of the C5aR gene has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of C5aR. A functional knock-out may also be achieved by the introduction of an anti-sense construct that blocks expression of the native genes (for example, see Li and Cohen (1996) Cell 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or repressor.

Identification and/or Evaluation of Ligands, Agonists, Inverse Agonists and/or Antagonists of C5aR Through use of the subject transgenic animals or cells derived therefrom, one can identify ligands or substrates that modulate phenomena associated with C5aR signalling. Depending on the particular assay, whole transgenic animals of the present invention may be used, or tissue, organs or cells derived therefrom. Cells may be freshly isolated from the transgenic animal, or may be immortalized in culture. Cells of particular interest are derived from tissue such as smooth muscle, endothelium, contractile muscle or heart.

The term "compound" as used herein describes any molecule, e.g. protein, small molecule, polynucleotide, or pharmaceutical, with the capability of preventing or suppressing the molecular and clinical phenomena associated with C5aR signalling.

Candidate compounds encompass numerous chemical classes, though in a preferred embodiment they are organic molecules, preferably small organic compounds having a molecular weight of more than 50 and less than about 2,500 daltons. Candidate compounds preferably comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

Candidate compounds are also found among biomolecules including, but not limited to saccharides, fatty acids, steroids, purines, pyrimidines, derivatives, structural analogs or combinations thereof.

Candidate compounds may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening may also be directed to known pharmacologically active compounds and chemical analogs thereof.

The candidate agent can be administered to the transgenic mammal of the invention (or cells derived from the transgenic mammal) in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Preferably, the in vivo screen will involve a number of animals receiving varying amounts and concentrations of the candidate compound (from no compound to an amount of compound that approaches an upper limit of the amount that can be delivered successfully to the animal), and may include delivery of the agent in different formulation. The compounds can be administered singly or can be combined in combinations of two or more, especially where administration of a combination of agents may result in a synergistic effect. The effect of agent administration upon the transgenic rodent can be monitored by conventional methodology.

The range of candidate compounds contemplated herein include C5aR inhibitory compounds or antagonists of a biological function of C5aR. In one embodiment, the compound is selected from the group consisting of: a peptide, including a peptide derived from C5aR or C5a or other non-C5aR peptides and capable of inhibiting, reducing or repressing a C5aR function, a C5aR dominant-negative mutant; a non peptide inhibitor of C5aR; an antibody or antibody fragment which binds to C5aR and inhibits a C5aR function; a small organic molecule, and nucleic acid, including nucleic acid encoding said peptide derived from C5aR or C5a or other non-C5aR peptide inhibitor, an antisense nucleic acid directed against C5aR-encoding mRNA, or an anti-C5aR ribozyme, or a small interfering RNA (RNAi) that targets C5aR gene expression. A number of these types of compound are discussed below.

Small Molecules

Candidate compounds encompass numerous chemical classes, though preferably they are organic molecules, preferably small organic compounds having a molecular weight of more than 100 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemicals groups. The candidate compounds often comprise cyclical carbon or heterocyclic structures and/or aromatic or polyaromatic structures substituted with one or more of the above functional groups. Candidate compounds are also found among biomolecules including peptides, saccharides, fatty acids, steroids, purines, pyrimidines and derivatives, structural analogs or combinations thereof. In fact, virtually any small organic molecule that is potentially capable of binding to a biological target molecule of interest may find use in the present invention provided that it is sufficiently soluble and stable in aqueous solutions to be tested for its ability to bind to the biological target molecule.

Candidate compounds are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological compounds may be subjected to directed or random chemical modifications, such as acylation, alkylation, esterification, amidification to produce structural analogs.

Protein or Peptide Inhibitors

In another embodiment, the candidate compounds are proteins. By "protein" in this context it is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homophenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or (L)-configuration. If non-naturally occurring side chains are used, non-amino acid substituents may be used, for example to prevent or retard in vivo degradations.

In a further preferred embodiment, the candidate compounds are naturally occurring proteins or fragments of naturally occurring proteins. Thus, for example, cellular extracts containing proteins, or random or directed digests of proteinaceous cellular extracts, may be used. In this way libraries of prokaryotic and eukaryotic proteins may be made. Particularly preferred in this embodiment are libraries of bacterial, fungal, viral, and mammalian proteins, with the latter being preferred, and human proteins being especially preferred.

In a further preferred embodiment, the candidate compounds are peptides of about 5 to about 30 amino acids in length, with peptides of about 5 to about 20 amino acids being preferred, and of about 7 to about 15 amino acids being particularly preferred. The peptides may be digests of naturally occurring proteins, random peptides, or "biased" random peptides. By "randomized" or grammatical equivalents herein is meant that each peptide consists of essentially random amino acids. Since generally these random peptides are chemically synthesized, they may incorporate any amino acid at any position. The synthetic process can be designed to generate randomized proteins to allow the formation of all or most of the possible combinations over the length of the sequence, thus forming a library of randomized candidate bioactive proteinaceous compounds.

Preparation and screening of combinatorial chemical libraries are well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487-493, Houghton et al. (1991) Nature, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) Proc. Nat. Acad. Sci. USA 90: 69096913), vinylogous polypeptides (Hagihara et al. (1992) J. Amer. Chem. Soc. 114: 6568), nonpeptidal peptidomimetics with a Beta D Glucose scaffolding (Hirschmann et al., (1992) J. Amer. Chem. Soc. 114: 92179218), analogous organic syntheses of small compound libraries (Chen et al. (1994) J. Amer. Chem. Soc. 116: 2661), oligocarbamates (Cho, et al., (1993) Science 261:1303), and/or peptidyl phosphonates (Campbell et al., (1994) J. Org. Chem. 59: 658). See, generally, Gordon et al., (1994) J. Med. Chem. 37:1385, nucleic acid libraries, peptide nucleic acid libraries (see, e.g., U.S. Pat. No. 5,539,083) antibody libraries (see, e.g., Vaughn et al. (1996) Nature Biotechnology, 14(3): 309-314), and PCT/US96/10287), carbohydrate libraries (see, e.g., Liang et al. (1996) Science, 274: 1520-1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

In one embodiment, peptidyl C5aR inhibitors are chemically or recombinantly synthesized as oligopeptides (usually 10-25 amino acids in length) derived from the C5aR or C5a sequence. Alternatively, C5aR or C5a fragments are produced by digestion of native or recombinantly produced C5aR or C5a by, for example, using a protease, e.g., trypsin, thermolysin, chymotrypsin, or pepsin. Computer analysis (using commercially available software, e.g. MacVector, Omega, PCGene, Molecular Simulation, Inc.) is used to identify proteolytic cleavage sites. The proteolytic or synthetic fragments can comprise as many amino acid residues as are necessary to partially or completely inhibit C5aR function. Preferred fragments will comprise at least 5, 10, 15, 20, 25, 30, 35, 40, 45, 50, 55, 60, 65, 70, 75, 80, 85, 90, 95, 100 or more amino acids in length.

Protein or peptide inhibitors may also be dominant-negative mutants of C5aR. The term "dominant-negative mutant" refers to a C5aR polypeptide that has been mutated from its natural state and that interacts with a protein that C5aR normally interacts with thereby preventing endogenous native C5aR from forming the interaction.

Anti-C5aR Antibodies

The term "antibody" as used in this invention includes intact molecules as well as fragments thereof, such as Fab, F(ab')$_2$, and Fv which are capable of binding an epitopic determinant of C5aR. These antibody fragments retain some ability to selectively bind with its antigen and are defined as follows:

(1) Fab, the fragment which contains a monovalent antigen-binding fragment of an antibody molecule can be produced by digestion of whole antibody with the enzyme papain to yield an intact light chain and a portion of one heavy chain;
(2) Fab', the fragment of an antibody molecule can be obtained by treating whole antibody with pepsin, followed by reduction, to yield an intact light chain and a portion of the heavy chain; two Fab' fragments are obtained per antibody molecule;
(3) F(ab')$_2$, the fragment of the antibody that can be obtained by treating whole antibody with the enzyme pepsin without subsequent reduction; F(ab')$_2$ is a dimer of two Fab' fragments held together by two disulfide bonds;
(4) Fv, defined as a genetically engineered fragment containing the variable region of the light chain and the variable region of the heavy chain expressed as two chains; and
(5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

Antibodies of the present invention can be prepared using intact C5aR or fragments thereof as the immunizing antigen. A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide may then be used to immunize the animal (e.g., a mouse or a rabbit).

If desired, polyclonal antibodies can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

Monoclonal antibodies may be prepared using any technique which provides for the production of antibody molecules by continuous cell lines in culture, such as, for example, the hybridoma technique, the human B-cell hybridoma technique, and the EBV-hybridoma technique (Kohler et al. Nature 256, 495-497, 1975; Kozbor et al., J. Immunol. Methods 81, 31-42, 1985; Cote et al., Proc. Natl. Acad. Sci. USA 80, 2026-2030, 1983; Cole et al., Mol. Cell Biol. 62, 109-120, 1984).

Methods known in the art allow antibodies exhibiting binding for C5aR to be identified and isolated from antibody expression libraries. For example, a method for the identification and isolation of an antibody binding domain which exhibits binding to C5aR is a bacteriophage vector system. This vector system has been used to express a combinatorial library of Fab fragments from the mouse antibody repertoire in *Escherichia coli* (Huse, et al., Science, 246:1275-1281, 1989) and from the human antibody repertoire (Mullinax, et al., Proc. Natl. Acad. Sci., 87:8095-8099, 1990). This methodology can also be applied to hybridoma cell lines expressing monoclonal antibodies with binding for a preselected ligand. Hybridomas which secrete a desired monoclonal antibody can be produced in various ways using techniques well understood by those having ordinary skill in the art and will not be repeated here. Details of these techniques are described in such references as Monoclonal Antibodies-Hybridomas: A New Dimension in Biological Analysis, Edited by Roger H. Kennett, et al., Plenum Press, 1980; and U.S. Pat. No. 4,172,124, incorporated by reference.

In addition, methods of producing chimeric or "humanized" antibodies are known in the art and include combining murine variable regions with human constant regions (Cabily, et al. Proc. Natl. Acad. Sci. USA, 81:3273, 1984), or by grafting the murine-antibody complementarity determining regions (CDRs) onto the human framework (Riechmann, et al., Nature 332:323, 1988).

Antisense Compounds

The term "antisense compounds" encompasses DNA or RNA molecules that are complementary to at least a portion of a target mRNA molecule (Izant and Weintraub, 1984; Izant and Weintraub, 1985) and capable of interfering with a post-transcriptional event such as mRNA translation. Antisense oligomers complementary to at least about 15 contiguous nucleotides of the target-encoding mRNA are preferred, since they are easily synthesized and are less likely to cause problems than larger molecules when introduced into the target mRNA producing cell. The use of antisense methods is well known in the art (Marcus-Sakura, 1988).

Catalytic RNA Molecules

The term catalytic RNA refers to an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T and U, as well as derivatives thereof. Derivatives of these bases are well known in the art.

Typically, the catalytic nucleic acid contains an antisense sequence for specific recognition of a target nucleic acid, and a nucleic acid cleaving enzymatic activity (also referred to herein as the "catalytic domain").

The types of ribozymes that are particularly useful in this invention are the hammerhead ribozyme (Haseloff and Gerlach 1988, Perriman et al, 1992) and the hairpin ribozyme (Shippy et al, 1999).

The ribozymes used in this invention can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette.

dsRNA dsRNA is particularly useful for specifically inhibiting the production of a particular protein. Although not wishing to be limited by theory, Dougherty and Parks (1995) have provided a model for the mechanism by which dsRNA can be used to reduce protein production. This model was modified and expanded by Waterhouse et al (1998). This technology relies on the presence of dsRNA molecules that contain a sequence that is essentially identical to the mRNA of the gene of interest. Conveniently, the dsRNA can be produced in a single open reading frame in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules targeted against genes of interest is well within the capacity of a person skilled in the art, particularly considering Dougherty and Parks (1995), Waterhouse et al (1998), WO 99/32619, WO 99/53050, WO 99/49029, and WO 01/34815.

As used herein, the terms "small interfering RNA", and "RNAi" refer to homologous double stranded RNA (dsRNA) that specifically targets a gene product, thereby resulting in a null or hypomorphic phenotype. Specifically, the dsRNA comprises two nucleotide sequences derived from the target RNA and having self-complementarity such that they can anneal, and interfere with expression of a target gene, presumably at the post-transcriptional level. RNAi molecules are described by Fire et al (1998) and reviewed by Sharp (1999).

Phenotypes Associated with C5aR Signalling

In the methods of the present invention, a putative compound is administered to the transgenic animal and a response of the transgenic animal to the putative compound is measured. Preferably, the response of the transgenic mammal is compared to the response of a "normal" or wild-type mouse or, alternatively, compared to a transgenic animal control (without administration of the compound).

Accordingly, in one aspect the present invention provides a method of identifying a compound that modulates C5aR activity, the method comprising (i) administering a candidate compound to a transgenic mammal of the present invention under conditions in which at least one phenotype associated with C5aR signalling is expressed; and (ii) monitoring development of the phenotype following administration of the compound.

The phenotype monitored may be any indicator of C5aR signalling, including the following:

(a) inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis);

(b) autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease;

(c) graft rejection (e.g., in transplantation), including allograft rejection or graft-versus-host disease;

(d) atherosclerosis;

(e) cancers with leukocyte infiltration of the skin or organs;

(f) diseases or conditions (including C5aR-mediated diseases or conditions), in which undesirable inflammatory responses are to be inhibited can be treated, including, but not limited to, reperfusion injury, stroke, adult respiratory distress syndrome, certain hematologic malignancies, cytokine-induced toxicity (e.g., septic shock, endotoxic shock), polymyositis, dermatomyositis, pemphigoid, Alzheimers Disease and granulomatous diseases including sarcoidosis.

Other phenotypes include immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; and immunosuppression due congenital deficiency in receptor function or other causes.

A number of in vivo models of inflammation are available and can be used to induce suitable C5aR associated phenotypes in transgenic mammals of the present invention. For example, rheumatoid arthritis can be evaluated using an animal (e.g. mouse) model of collagen-induced arthritis (Trentham et al (1977) J Exp Med 146: 857-868), K/BxN serum-induced arthritis (Kouskoff et al (1996) Cell 87:811-822), antigen-induced arthritis, or adjuvant-induced arthritis (Pearson C M (1956) Proc Soc. Expe Biblo Med 91:95-101).

Further examples of suitable animal models include: cecal ligation puncture (CLP) model of sepsis (Huber-Lang, M. S., et al. (2002) Faseb J 16(12): 1567-74); rat model of RA (Woodruff, T. M., et al. (2002) Arthritis Rheum 46(9): 2476-85); porcine model of sepsis (Mohr, M., et al. (1998) Eur J Clin Invest 28(3): 227-34); immune complex-induced lung disease; pancreatitis associated lung injury (Bhatia, M., et al. (2001) Am J Physiol Gastrointest Liver Physiol 280(5): G974-8); acute lung injury; renal ischaemia-reperfusion injury; collagen-induced arthritis; and experimental airway disease (asthma like model).

In another example, leukocyte infiltration upon intradermal injection of a candidate compound can be monitored (see e.g., Van Damme, J. et al., J. Exp. Med., 176: 59-65 (1992); Zachariae, C. O. C. et al., J. Exp. Med. 171: 2177-2182 (1990); Jose, P. J. et al., J. Exp. Med. 179: 881-887 (1994)). In one embodiment, skin biopsies are assessed histologically for infiltration of leukocytes (e.g., eosinophils, granulocytes). A decrease of the extent of infiltration in the presence of the candidate compound as compared with the extent of infiltration in the absence of the candidate compound is indicative of inhibition of C5aR signalling.

Examples of preferred phenotypes are discussed briefly below.

Autoimmune Diseases (Including Rheumatoid Arthritis)

Autoimmune diseases afflict 5-8% of the population. Immune complexes (IC) play an integral role in the pathogenesis of several of autoimmune diseases including rheumatoid (RA) arthritis, systemic lupus erythematosus (SLE), glomerulonephritis and immune vasculitis. While ICs initiate the autoimmune reaction other important factors contributing to disease severity include the complement system, Fcg receptors and neutrophils. It is now recognised that the main contribution of complement to IC inflammation is through C5aR signalling. ICs activate both the classic and alternative complement pathways. C5a, released by cleavage of C5 during complement activation is a powerful chemoattractant of neutrophils, monocytes and macrophages. C5a binding to C5aR initiates a series of events, including FcgR activation on macrophages (up-regulating activating FcgRIOII and FcgRI and down-regulating inhibitory FcgRIIB) causing more chemotactic mediators (e.g. CXC chemokines) to be released and further orchestration of the inflammatory response.

The importance of C5a/C5aR has been demonstrated in various model systems of immune complex inflammation. For example, C5a has been shown to initiate the inflammatory cascade in a mouse peritonitis model of the reverse passive Arthus reaction (Godau J, et al, J Immunol 173, 3437 (2004)). C5a has also been shown to regulate FcgRs in IC-induced lung disease (Shushakova N J, et al, J Clin Invest, 110, 1823-1830 (2002)). Further, C5aR knock-out mice do not develop inflammation in the Benoist-Mathis KRNxNOD serum transfer model of Rheumatoid Arthritis (Ji H, et al, Immunity 16, 157 (2002)) or in an anti-collagen antibody induced arthritis model (Grant E P, et al, J Exp Med 196, 1461 (2002))

Sepsis

Sepsis is a severe illness caused by overwhelming infection of the bloodstream by toxin-producing bacteria. It is has been recognized that the innate immune system can be perturbed during sepsis, as evidenced by extensive activation of the inflammatory, complement, and clotting systems, together with the appearance in plasma of cytokines and chemokines. This "cytokine storm" as it has been termed unleashes numerous inflammatory mediators that contribute to multiple-organ dysfunction or failure and death.

Recent reviews of sepsis reflect on past attempts at finding treatments for this disease and suggest future directions (Crowther and Marshall (2001) Jama 286(15): 1894-6; Cohen, J. (2002) Nature 420(6917):885-91; Cross and Opal (2003) Ann Intern Med 138(6): 502-5).

Hotchkiss and Karl (N Engl J Med 348(2):138-50, 2003) speculate that the efficacy shown by the anti-coagulant recombinant activated protein C in reducing mortality in sepsis may be due in part to its anti-inflammatory effects. Some of the effects (direct and indirect) of activated protein C are blocking production of cytokines, blocking cell adhesion, inhibiting neutrophil recruitment, mast cell degranulation and platelet activation. C5a mediates leukocyte chemotaxis, release of histamine from mast cells, enhancement of neutrophil-endothelial cell adhesion and induction of cytokine production through binding to the C5a receptor.

During sepsis in humans, unregulated activation of the complement system results in excessive generation of anaphylatoxins, especially C3a and C5a and ensuing dysfunction of neutrophils. In later stages of sepsis, neutrophils have suppressed chemotactic responsiveness, depressed enzyme release, alterations of intracellular pH and a defective respiratory burst (diminished production of reactive oxygen species, especially $H_2O_2$), leading to impaired bactericidal activity. These defects have been shown to be C5a dependent. During experimental sepsis blood neutrophils have a greatly diminished ability to bind C5a, have impaired chemotactic responses to C5a and a loss of $H_2O_2$ production. These defects can be prevented in CLP induced sepsis by treating animals with anti-C5a antibodies. This treatment reduced bacteremia and greatly improved survival. This indicates that sepsis induces excessive generation of C5a, which, in turn, leads to serious functional defects in neutrophils.

Antibodies to C5aR can also protect against death from sepsis in animal models. It has been shown that C5aR immunoreactivity and mRNA expression both are increased in epithelial cells of lung, kidney, liver, heart and thymus early in experimental sepsis.

Mice injected at the start of CLP with antibodies to C5aR showed dramatically improved survival when compared with animals receiving nonspecific IgG. In anti-C5aR-treated mice, serum levels of IL-6 and TNF-α and bacterial counts in various organs were significantly reduced during CLP when compared with control CLP animals. These studies demonstrated that blockade of C5aR is highly protective from the lethal outcome of sepsis.

It has been suggested that it is the location of C5a that may be critical in terms of its potential to protect or harm. Local generation of C5a in tissues is essential for early control of infection. A C5a gradient is established causing leukocyte chemotaxis. At higher C5a concentrations chemotaxis is arrested and the cells produce their toxic oxygen burst. In sepsis, diffuse complement activation in the blood leads to an excess of diffuse intravascular C5a which cripples neutrophils allowing unrestrained proliferation of bacteria. Simultaneously sequestration of the neutrophils in the microcirculation injures the lung, kidney and liver. In this model the C5aR on leukocytes rather than the receptor on the epithelial cells of the liver, lung etc. may be critical. Intervention, by way of C5aR antagonists may prove therapeutically valuable.

Ischaemia—Reperfusion Injury (IR)

The complement system is an important mediator of inflammatory tissue damage in various diseases including ischaemia-reperfusion (IR) injury.

The relative roles of C5a and the membrane attack complex C5b-9 in mediating IR injury seem to vary. In some models C5a is the important mediator. Antagonists of C5aR protect mice and rats against IR injury in small intestine and kidney (Heller et al. (1999) J Immunol 163(2): 985-94; Arumugam et al. (2003) Kidney Int 63(1): 134-42; Arumugam et al. (2002) J Surg Res 103(2):260-7). In a porcine myocardial IR injury model a C5aR antagonist reduced infarct size markedly (Riley et al. (2000) J Thorac Cardiovasc Surg 120(2): 350-8).

Studies with antibodies to C5 also demonstrate similar reductions in IR injury (Fitch et al. (1999) Circulation 100 (25):2499-506; de Vries et al (2003) Transplantation 75(3): 375-82).

Clinical and experimental studies have shown that IR of organs such as the kidney, liver, lungs and heart induces a rapid release of various cytokines. While many of these molecules decrease in level after reperfusion, IL-8 significantly increases. IL-8 is a potent neutrophil chemoattractant. Levels of IL-8 negatively correlate with lung fimction and high levels are associated with increased risk of death in lung transplantation. Intravenous administration of anti-IL-8 antibodies at the beginning of reperfusion markedly reduces lung injury and neutrophil infiltration (de Perrot et al (2003) Am J Respir Crit Care Med 167(4):490-511).

Evidence shows that IR injury occurs in a biphasic pattern. Macrophages activated during ischaemia mediate the early phase of injury whereas neutrophils and lymphocytes are primarily involved in the second, delayed phase. The recruitment of neutrophils and lymphocytes results from the release of cytokines before and after reperfusion.

Since C5a is a potent chemoattractant for various myeloid cells including macrophages and neutrophils and also induces cytokine production it is envisaged that blocking C5aR with specific antibodies could be beneficial in preventing IL-8 release and neutrophil migration and thus reduce IR injury.

Acute Respiratory Distress Syndrome (ARDS) & Acute Lung Injury (ALI)

ARDS and ALI are syndromes that result from pulmonary edema and inflammation. The development of ARDS/ALI is associated with several clinical disorders including pulmonary injury from pneumonia infection, aspiration of gastric contents, trauma, sepsis, acute pancreatitis, drug overdose and cardiopulmonary bypass. Sepsis is the leading cause of ARDS/ALI. As with IR, the inflammatory response in ALI is associated with recruitment of large numbers of neutrophils and monocytes into the distal airspaces of the lung. Proinflammatory molecules such as cytokines, oxygen radicals and proteases play a role and excessive inflammation may worsen ARDS/ALI (Ware and Matthay (2000) N Engl J Med 342 (18): 1334-49; Brower et al. (2001) Chest 120(4): 1347-67).

It has been suggested that anti-inflammatory strategies to reduce the number of neutrophils migrating into extravascular spaces in the lung, to reduce neutrophil adhesion to the lung endothelium, and to reduce release of chemotactic factors could be beneficial (Brower et al. (2001) Chest 120(4): 1347-67).

Studies of patients with ARDS reveals that high levels of IL-8 are present in the BAL fluid or pulmonary edema fluid in the early phases of the disease. Furthermore, antibodies that neutralise IL-8 reduced lung injury in a rabbit model (Brower et al. (2001) Chest 120(4): 1347-67).

For ARDS and ALI blocking C5aR may also be a therapeutically viable approach. C5a is a potent chemotactic molecule and stimulator of cytokine release. Studies described above which used molecules that antagonise C5a or C5aR demonstrated reduction in injury in various models of inflammation.

Production of Compounds Identified in the Screening Methods of the Invention

In one embodiment of the invention, the subject method further comprises producing or synthesizing the compound that is tested on the genetically modified animal.

Peptidyl compounds are conveniently made by standard peptide synthesis, such as the Merrifield method of synthesis (Merrifield, *J Am Chem Soc,* 85,:2149-2154, 1963) and the myriad of available improvements on that technology (see e.g., Synthetic Peptides: A User's Guide, Grant, ed. (1992) W.H. Freeman & Co., New York, pp. 382; Jones (1994) The Chemical Synthesis of Peptides, Clarendon Press, Oxford, pp. 230.); Barany, G. and Merrifield, R. B. (1979) in *The Peptides* (Gross, E. and Meienhofer, J. eds.), vol. 2, pp. 1-284, Academic Press, New York; Wünsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart; Bodanszky, M. (1984) *Principles of Peptide Synthesis*, Springer-Verlag, Heidelberg; Bodanszky, M. & Bodanszky, A. (1984) *The Practice of Peptide Synthesis, Springer-Verlag*, Heidelberg; Bodanszky, M. (1985) *Int. J. Peptide Protein Res.* 25, 449-474.

Preferably, the peptide is synthesized on a solid phase support, such as, for example, a polystyrene gel bead comprising polystyrene cross-linked with divinylbenzene, preferably 1% (w.w) divinylbenzene, which is further swollen using lipophilic solvent, such as, for example dichloromethane or dimethylformamide (DMF). The polystyrene can be functionalized by addition of chloromethane or amino methyl groups.

Alternatively, cross-linked and functionalized polydimethyl-acrylamide gel can be used once swollen and solvated using DMF or dipolar aprotic solvent. Other solid phase supports known to those skilled in the art can also be used for peptide synthesis, such as, for example, polyethylene glycol-derived bead produced by grafting polyethylene glycol to the surface of inert polystyrene beads. Preferred commercially available solid phase supports include PAL-PEG-PS, PAC-PEG-PS, KA, KR, or TGR (Applied Biosystems, CA 94404, USA).

For solid phase peptide synthesis, blocking groups that are stable to the repeated treatments necessary for removal of the amino blocking group of the growing peptide chain and for repeated amino acid couplings, are used for protecting the amino acid side-chains during synthesis and for masking undesired reactivity of the α-amino, carboxyl or side chain functional groups. Blocking groups (also called protecting groups or masking groups) thus protect the amino group of the amino acid having an activated carboxyl group that is involved in the coupling reaction, or protect the carboxyl group of the amino acid having an acylated amino group that is involved in the coupling reaction.

During synthesis, coupling occurs following removal of a blocking group without the disruption of a peptide bond, or any protecting group attached to another part of the peptide.

Additionally, the peptide-resin anchorage that protects the C-terminus of the peptide is protected throughout the synthetic process until cleavage from the resin is required. Accordingly, by the judicious selection of orthogonally protected α-amino acids, amino acids are added at desired locations to a growing peptide whilst it is still attached to the resin.

Preferred amino blocking groups are easily removable but sufficiently stable to survive conditions for the coupling reaction and other manipulations, such as, for example, modifications to the side-chain groups. In one embodiment, amino blocking groups are selected from the group consisting of: (i) a benzyloxycarbonyl group (Z or carbocenzoxy) that is removed easily by catalytic hydrogenation at room temperature and ordinary pressure, or using sodium in liquid ammonia and hydrobromic acid in acetic acid; (ii) a urethane derivative; (iii) a t-Butoxycarbonyl group (Boc) that is introduced using t-butoxycarbonyl azide or di-tert-butyldicarbonate and removed using mild acid such as, for example, trifluoroacetic acid (50% TFA in dichloromethane), or HCl in acetic acid/dioxane/ethylacetate; (iv) a 9-fluorenylmethyloxycarbonyl group (Fmoc) that is cleaved under mildly basic, non-hydrolytic conditions, such as, for example, using a primary or secondary amine (eg. 20% piperidine in dimethyl formamide); (v) a 2-(4-biphenylyl)propyl(2)oxycarbonyl group (Bpoc); (vi) a 2-nitro-phenylsulfenyl group (Nps); and (vii) a dithia-succionyl group (Dts). Boc is widely used to protect the N-terminus in Fmoc chemistry, or Fmoc is widely used to protect the N-terminus in Boc chemistry.

Side chain-protecting groups will vary for the functional side chains of the amino acids forming the peptide being synthesized. Side-chain protecting groups are generally based on the Bzl group or the tBu group. Amino acids having alcohols or carboxylic acids in the side-chain are protected as Bzl ethers, Bzl esters, cHex esters, tBu ethers, or tBu esters. Side-chain protection of Fmoc amino acids requires blocking groups that are ideally base stable and weak acid (TFA) labile. Many different protecting groups for peptide synthesis have been described (see The Peptides, Gross et al. eds., Vol. 3, Academic Press, New York, 1981). For example, the 4-methoxy-2,3,6-trimethylphenylsulfonyl (Nd-Mtr) group is useful for Arginine side-chain protection, however deprotection of Arg(Mtr) requires prolonged TFA treatment. A number of soft acid (TFA, thalium (III) trifluoroacetate/TFA) labile groups, or TFA stable but thalium (III) trifluoroacetate/TFA labile groups, or soft acid stable groups are used to protect Cystine.

The two most widely used protection strategies are the Boc/Bzl- and the Fmoc/tBu-strategies. In Boc/Bzl, Boc is used for amino protection and the side-chains of the various amino acids are protected using Bzl- or cHex-based protecting groups. A Boc group is stable under catalytic hydrogenation conditions and is used orthogonally along with a Z group for protection of many side chain groups. In Fmoc/tBu, Fmoc is used for amino protection and the side-chains are protected with tBu-based protecting groups.

Alternatively, the peptidyl compound is produced by the recombinant expression of nucleic acid encoding the amino acid sequence of said peptide. Random peptide-encoding libraries are particularly preferred for such purposes, because they provide a wide range of different compounds to test. Alternatively, naturally-occurring nucleic acids can be screened. According to this embodiment, nucleic acid encoding the peptidyl compound is produced by standard oligonucleotide synthesis or derived from a natural source and cloned into a suitable expression vector in operable connection with a promoter or other regulatory sequence capable of regulating expression in a cell-free system or cellular system.

Oligonucleotides are preferably synthesized with linker or adaptor sequences at the 5'- and 3'-ends to facilitate subsequent cloning into a suitable vector system using standard techniques.

Placing a nucleic acid molecule under the regulatory control of, i.e., "in operable connection with", a promoter sequence means positioning said molecule such that expression is controlled by the promoter sequence, generally by positioning the promoter 5' (upstream) of the peptide-encoding sequence.

The prerequisite for producing intact peptides in bacteria such as E. coli is the use of a strong promoter with an effective ribosome binding site. Typical promoters suitable for expression in bacterial cells such as E. coli include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in E. coli are well-known in the art and are described, for example, in Ausubel et al (In: Current Protocols in Molecular Biology. Wiley Interscience, ISBN 047150338, 1987) or Sambrook et al (In: Molecular cloning, A laboratory manual, second edition, Cold Spring Harbor Laboratory, Cold Spring Harbor, N.Y., 1989). Numerous plasmids with suitable promoter sequences for expression in bacteria and efficient ribosome binding sites have been described, such as for example, pKC30 ($\lambda_L$: Shimatake and Rosenberg, Nature 292, 128, 1981); pKK173-3 (tac: Amann and Brosius, Gene 40, 183, 1985), pET-3 (T7: Studier and Moffat, J. Mol. Biol. 189, 113, 1986); the pBAD/TOPO or pBAD/Thio-TOPO series of vectors containing an arabinose-inducible promoter (Invitrogen, Carlsbad, Calif.), the latter of which is designed to also produce fusion proteins with thioredoxin to enhance solubility of the expressed protein; the pFLEX series of expression vectors (Pfizer Inc., CT, USA); or the pQE series of expression vectors (Qiagen, Calif.), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (eg. 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRαtkneo (Muller et al., Mol. Cell. Biol., 11, 1785, 1991). The vector pcDNA 3.1 myc-His (Invitrogen) is particularly preferred for expressing peptides in a secreted form in 293T cells, wherein the expressed peptide or protein can be purified free of con-specific proteins, using standard affinity techniques that employ a Nickel column to bind the protein via the His tag.

A wide range of additional host/vector systems suitable for expressing peptides are available publicly, and described, for example, in Sambrook et al (In: Molecular cloning, A laboratory manual, second edition, Cold Spring Harbor Laboratory, Cold Spring Harbor, N.Y., 1989).

Means for introducing the nucleic acid or a gene construct comprising same into a cell for expression are well-known to those skilled in the art. The technique used for a given organism depends on the known successful techniques. Means for introducing recombinant DNA into animal cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

Techniques for synthesizing small organic compounds will vary considerably depending upon the compound, however such methods will be well known to those skilled in the art. In one embodiment, informatics is used to select suitable chemical building blocks from known compounds, for producing a combinatorial library. For example, QSAR(Quantitative Structure Activity Relationship) modelling approach uses linear regressions or regression trees of compound structures to determine suitability. The software of the Chemical Computing Group, Inc.(Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and logP (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, information from known appetite suppressants and non-suppressants, including lead compounds identified in initial screens, can be used to expand the list of compounds being screened to thereby identify highly active compounds.

In one embodiment, the subject method further comprises formulating the identified compound for administration to a non-human animal or a human. The formulations can be suitable for administration by injection by a subcutaneous, intravenous, intranasal, or intraperitoneal route. Alternatively, they can be suitable for oral administration in the form of feed additives, tablets, troches, etc.

The compounds are conveniently formulated in a suitable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, antioxidants, chelating agents and inert gases. The pH and exact concentration of the various components the formulation suitable for administration to the animal are adjusted according to routine skills in the art. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Optionally, the formulation will also include a carrier, such as, for example, bovine serum albumin (BSA), keyhole limpet hemocyanin (KLH), ovalbumin, mouse serum albumin, rabbit serum albumin and the like. Means for conjugating peptides to carrier proteins are also well known in the art and include glutaraldehyde, m-maleimidobencoyl-N-hydroxysuccinimide ester, carbodiimide and bis-biazotized benzidine.

The present invention will now be illustrated by the following Examples, which are not intended to be limiting in any way. The teachings of all references cited herein are incorporated herein by reference.

Example 1

Generation of Targeting Construct for Producing Human C5aR Knock-In Mouse

To produce a mutant mouse strain by homologous recombination, two major elements are needed. An embryonic stem (ES) cell line capable of contributing to the germ line, and a targeting construct containing target-gene sequences with the desired mutation. Maintaining ES cells in their undifferentiated is accomplished by growing cells on a layer of feeder cells. The targeting construct is then transfected into cultured ES cells. ES cell lines are derived from the inner cell mass of a blastocyst-stage embryo. Homologous recombination occurs in a small number of the transfected cells, resulting in introduction of the mutation present in the targeting construct into the target gene.

Once identified, mutant ES cell clones can be microinjected into a normal blastocyst in order to produce a chimeric mouse. Because many ES cell lines retain the ability to differentiate into every cell type present in the mouse, the chimera can have tissues, including the germ line, with contribution from both the normal blastocyst and the mutant ES cells. Breeding germ-line chimeras yields animals that are heterozygous for the mutation introduced into the ES cell, and they can be interbred to produce homozygous mutant mice.

As shown in FIG. 1, the targeting construct used to replace the endogenous mouse C5aR sequence with the human C5aR sequence contains two regions of homology to the target gene located on either side of a positive selectable marker (PGK-Neo, a hybrid gene consisting of the phosphoglycerate kinase I promoter which drives the neomycin phosphotransferase gene). Homologous recombination proceeds by a double cross-over event that replaces the target-gene sequences with the replacement-construct sequences. Because no duplication of sequences occurs, the normal gene cannot be regenerated.

When the targeting construct is linearized, the neo gene is flanked by two regions of homology to the target gene. Selection of the cells using drugs (e.g., G418) eliminates the great majority of cells that have not stably incorporated the construct.

Although many gene inactivation approaches involving homologous recombination still use constructs that leave the positive selectable marker in the genomic DNA, it has become increasingly clear that this can cause a number of unanticipated effects. For example, the presence of the neo gene, often with its own promoter, can alter the expression of neighbouring loci. This can be a particular problem in gene clusters where neighbouring genes are in the same family, since the genes affected may have similar or identical functions. As a result, slight differences in targeting constructs have led to marked differences in phenotype.

Figure 2:
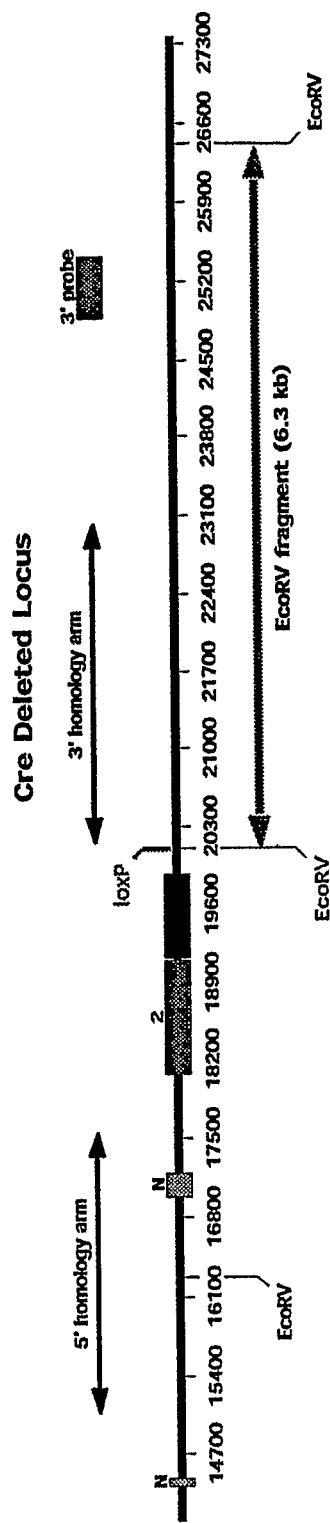
FIG. 2: Diagram showing transgenic mouse C5aR locus after deletion of the PGKneo gene by Cre recombinase.

For this reason, the targeting construct exemplified herein includes loxP sites flanking the PGK-neo gene, so that the selectable marker can be removed after targeting by transient expression of the Cre recombinase. This will leave the small loxP site in the genomic DNA, but the construct can be engineered so that this is in an innocuous location (FIG. 2). Although theoretically even a loxP site could cause alterations in the expression of neighboring genes, no such cases have yet been reported. The efficiency of Cre recombination from transient expression reported in the literature varies widely, from ~2% to ~15%. This rate should be distinguished from the efficiency of Cre recombination in vivo, where the expression of Cre is derived from sequences integrated into the genome and therefore will show longer-lasting expression in nearly all cases.

SEQ ID NO:1 shows the mouse genomic DNA sequence (~22 kb) encompassing the C5aR (C5r1) gene. SEQ ID NO:2 shows the human C5aR cDNA sequence and SEQ ID NO:3 shows the human C5aR protein sequence.

The mouse genomic region as shown in SEQ ID NO:1 (the target locus) is characterized as follows:

exon 1: nucleotides 757-784 (5' untranslated region)

exon 2: nucleotides 1048-1152 (5' untranslated region plus start codon)

exon 3: nucleotides 10726-11778 (all coding sequence except ATG).

Figure 3:
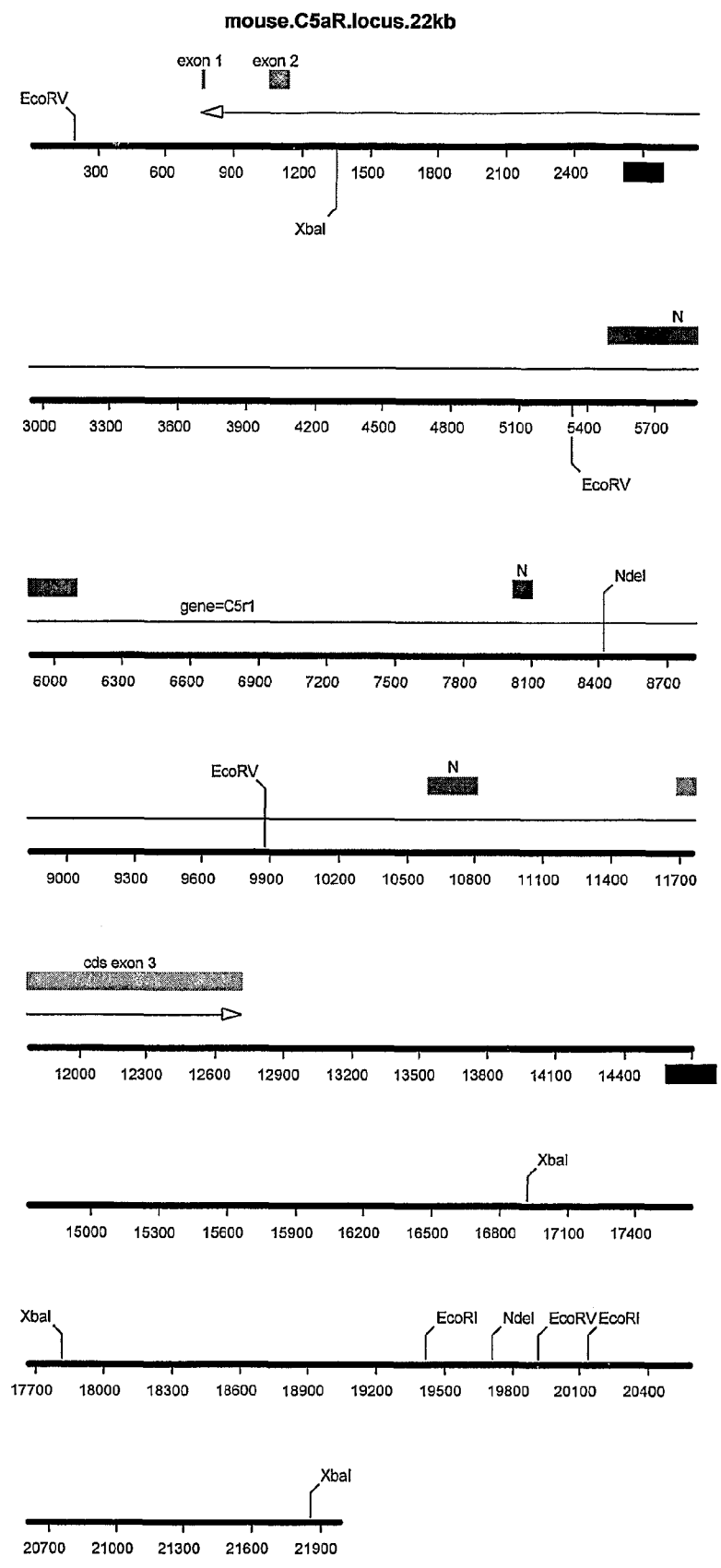
FIG. 3: Diagram showing selected restriction sites and mouse C5aR (C5r1) gene exons.

FIG. 3 shows a restriction map of the 22 kb sequence shown in SEQ ID NO:1. The relevant restriction sites are as follows:

| Enzyme | #Cuts | Positions: | | | |
|--------|-------|------|------|------|------|
| EcoRI  | 2     | 18462 | 19176 |      |      |
| EcoRV  | 4     | 199   | 5337  | 9151 | 18964 |
| NdeI   | 2     | 7698  | 18758 |      |      |
| XbaI   | 4     | 1351  | 15968 | 16852 | 20902 |

The targeting vector used to generate the knock-in mice includes regions homologous to approximately 3 kb genomic DNA either side of exon 3 (i.e. from about nucleotides 7377-15045 as shown in SEQ ID NO:1). In particular, the targeting vector comprised the region from about nucleotides 7377-15045 of SEQ ID NO:1 except that nucleotides 10726-11778 were replaced by nucleotides 28 to 1077 of SEQ ID NO:2.

This means that following integration, the endogenous mouse exons 1 and 2 remain in the transgenic mammal but exon 3 of the mouse locus has been replaced with a sequence encoding human C5aR.

Example 2

Transfection and Identification of Mouse Embryonic Stem Cells Containing the Human C5aR Gene A basic protocol for the culture of embryonic stem (ES) cells and for introducing the targeting construct into ES cells is provided below. This protocol also outlines the method for identifying clones in which the target gene has been altered by homologous recombination. The resulting homologous recombinants are heterozygous for human C5aR and can be used to produce transgenic mice homozygous for the human C5aR gene. In this example the ES cells were derived from C57BL/6 mice.

Materials

Targeting construct
Embryonic stem (ES) cells
ES/LIF medium
Trypsin/EDTA: 0.25% (w/v) trypsin/1 mM EDTA (20 mM HEPES, pH 7.3, optional)
ES medium
Electroporation buffer
G418
Freezing medium
Digestion buffer
Saturated NaCl
1% agarose gel Transfect Construct and Select ES Cells 1. Culture ES cells in ES/LIF medium. Passage cells every 2 to 3 days by seeding a 100-mm gelatin-coated tissue culture plate with $1-2 \times 10^6$ cells/plate. Leukemia inhibitory factor (LIF) prevents ES cells from differentiating. Passaging cells at a higher density may be preferable if blastocyst injection of the cells is planned (e.g., $1.5 \times 10^6$ cells per 25-$cm^2$ flask).

2. Harvest $\sim 5 \times 10^6$ to $1 \times 10^7$ cells by adding trypsin/EDTA and incubating for ~5 min until cells are freed from the plate surface. Dissociate to single cells by pipetting up and down five to ten times. Add 5 ml ES medium. Pellet cells and resuspend the cell pellet in 1 ml electroporation buffer in the same tube. Typically, $10^7$ cells can be obtained from a near-confluent 100-mm tissue culture plate.

3. Add 1 pmol linearized, sterile construct DNA.

4. Electroporate the mixture at 450 V and 250 uF in a 4-mm electroporation cuvette. Incubate 10 min at room temperature. Many electroporation conditions can be used with ES cells.

5. Plate cells in ES medium at $\sim 2 \times 10^6$ cells per 100-mm gelatin-coated tissue culture plate. Incubate 24 hr.

6. Begin selection by changing ES medium to ES/LIF medium and adding G418 to 0.2 mg/ml and GANC to 2 uM (final).

7. Continue incubation, changing medium daily using ES/LIF medium and adding G418 (0.2 mg/ml final), until single, isolated colonies are visible (typically 1 week after electroporation). Remove an individual colony from the plate using an autoclaved pipet tip, and place in a 35-ul drop of trypsin/EDTA for 5 min. Pipet up and down about five times to dissociate cells. Transfer cells to a well of a gelatin-coated 24-well microtiter plate containing 1 ml ES/LIF medium.

8. Incubate until colonies are visible, but the cells are not differentiating (typically 3 to 4 days). Passage half of the cells to a well of a clean gelatin-coated 24-well microtiter plate.

Add the remaining cells to 0.5 ml freezing medium and place at −70° C. Freeze overnight, then transfer to liquid nitrogen. Undifferentiated cells grow in smooth, round colonies. Differentiated cells are flatter with distinct intercellular boundaries. Proceed immediately to step 9 after placing half the cells in the freezer.

Screen for Homologous Recombinants

9. Incubate ES cells in 24-well microtiter plate (step 14) to near confluence (usually 2 to 3 days). Because it is not critical to prevent differentiation of the ES cells at this stage, LIF can be omitted from the culture medium; however, the presence of LIF may help to maintain cell growth.

10. Add 300 ul digestion buffer to each well. Transfer well contents to a 1.5-ml microcentrifuge tube, and incubate overnight at 55° C.

11. Add 150 ul saturated NaCl and vortex vigorously (the solution will turn milky white). Add 2 vol of 95% ethanol (the solution will turn clear except for precipitated DNA). Some investigators precipitate the DNA using 2 vol ethanol (or 1 vol isopropanol) without adding salt. However, the DNA pellet resuspends more easily if salt is added.

12. Resuspend DNA pellet in 50 ul water. Determine DNA concentration by measuring the absorbance at 260 nm.

13. Digest 10 ug DNA (or 10 ul if DNA concentration was not determined) with the appropriate restriction enzyme.

14. Fractionate the digested DNA on a 1% agarose gel. Transfer to a nylon membrane, and hybridize by Southern blotting to a suitable target-gene hybridization probe to distinguish the unaltered target gene from a target gene that has undergone homologous recombination.

15. Select ES cell colonies that show two hybridizing fragments of approximately equal intensity—one fragment of the predicted size for the unaltered target gene and one fragment of the predicted size for a target gene that has undergone homologous recombination. If the two fragments are of unequal hybridization intensity, the cell population may not be clonal. Freeze cells and store in liquid nitrogen.

A total of 672 colonies of ES cells transfected with the hC5aR targeting construct were screened for homologous recombination between the targeting construct and the mouse genome.

DNA extracted from ES cell colonies was digested with EcoRV or XbaI and electrophoresed through an agarose gel. The DNA was transferred to a filter (by the Southern method) and hybridised to $^{32}$P-labelled 5' probe or 3' probe DNA using standard conditions. After washing, the filter was exposed to X-ray film. This screening yielded three colonies containing the human C5aR gene. Two of these colonies (5H1 and 6C8) were identified as having a correctly integrated human C5aR gene in the mouse C5aR gene locus (data not shown).

Example 3

Implantation of ES Cells, Generation of Chimeras and Germline Transmission of the Human C5aR Gene The standard method for generating chimeras with ES cells uses 3.5-day-old mouse embryos (blastocysts). Embryos at this stage have a large fluid-filled cavity into which ES cells can be placed by injection. Blastocysts have already moved out of the oviducts and are found in the uterine horns. For injections, they must be harvested prior to hatching (loss of zona pellucida) and attachment to the uterine wall. Various mice strains are used to generate blastocysts for ES cell injections. In this example mouse strain Balb/c was used to generate blastocysts. This strain yields reasonable numbers of embryos. It tends to produce high-grade chimeras that can be easily distinguished by coat color when used with ES cells derived from a variety of C57BL/6 sub-strains.

ES cells from colonies 5H1 and 6C8 were injected into ~200 blastocysts. Blastocycts were implanted into pseudo-pregnant female mice. Some 17 coat-colour chimeras were born with between 5 and 50% black fur. The 13 male chimeras were mated with C57BL/6 females and produced some 300 pups. Germline transmission of the human C5aR gene was observed in 19 pups from 5 chimera×C57BL/6 mating pairs.

The presence of the human C5aR locus was confirmed by Southern blotting. Genomic DNA extracted from mouse tail was digested with EcoRV, electrophoresed and hybridised to the 3' probe. The filter was subsequently stripped and reprobed with the Neo probe. A number of mice were shown to contain the C5aR gene. The genotype of these mice was designated hC5aRfloxed(neoR)/wt (abbreviated H5Rf/+).

Example 4

Breeding and Identification of Mice Homozygous for the Human C5aR Gene

A generation H5Rf/+ mice were mated with C57BL/6 Cre deleter mice to remove the neoR marker gene thus generating H5R/wt/Cre mice. The H5R/wt/Cre mice were mated with C57BL/6 mice to remove Cre gene thus generating heterozygous H5R/wt mice (H5R/+). Matings between H5R/+ mice produced H5R/H5R homozygous knock-in mice. Some H5Rf/+×H5Rf/+ matings were also set up and generated H5Rf/H5Rf homozygotes.

Confirmation that mice carry the human C5aR gene was made using a PCR-based genotyping assay. The Southern blot genotype assay used above to identify mice carrying the human C5aR gene was based on hybridization with a mouse-specific DNA probe (not a human C5aR gene specific probe). The PCR assay described below utilized primers that specifically amplify human or mouse C5aR gene sequences.

Preparation of Tail DNA 3 mm tail tips were placed in 1.5 ml sterile eppendorf tubes and incubated overnight at 65° C. in 200 ul of DNA isolation buffer (67 mM Tris-Cl pH 8.0 (Calbiochem), 16.6 mM ammonium sulphate (Sigma), 6.5 mM magnesium chloride (Promega), 1% β-mercaptoethanol (ICN Biomedical) and 0.05% Triton X100 (Sigma)). The supernatant was transferred to a new 1.5 ml tube containing 500 ul 100% ethanol (UNIVAR), mixed and incubated for 2 hours at −20° C., then centrifuged for 15 minutes at 4° C. 13,000 rpm (Labofuge 400R, Heraeus Instruments) to precipitate purified genomic DNA. The DNA pellet was washed in 70% ethanol and allowed to dry before being resuspended in 50 ul distilled water. A 1 ul aliquot was used as the DNA template in the following PCR assay.

PCR to Amplify Human and Mouse C5aR Genes

Each PCR reaction contained 5 ul of magnesium free 10×PCR buffer, 5 ul of 25 mM magnesium chloride, 0.5 ul Taq DNA polymerase (2.5 units/ul), 1 ul 10 mM dNTPs (Promega), 1 ul of each 10 mM oligonucleotide primer (F1C, R2a, F3 C and R4C), 1 ul template DNA. The total volume was made up to 50 ul with distilled water. The oligonucleotide primers used were:

```
5'-TGGACTACAGCCACGACAAACG-3'  (F1C)    (SEQ ID NO: 4)
and
5'-AGGAAGGACATCATTATCCCCG-3'  (R2a),   (SEQ ID NO: 5)
``` both specific for the human C5aR exon 3; and,

```
5'-CACCAGCCCCGAGATTTTTC-3'    (F3C)    (SEQ ID NO: 6)
and
5'-TCAGAAACCAGATGGCGT-3'      (R4C),   (SEQ ID NO: 7)
``` both specific for the mouse C5aR gene.

The target sequences were then amplified using a PCR System 2700 thermal cycler (Applied Biosystems). PCR began with a 5 min 95° C. denaturation step, followed by 25 cycles of three steps: 95° C. for 30 sec, 60° C. for 30 sec and 72° C. for 60 sec. A final extension step: 5 min at 72° C. was followed by storage at 4° C.

Gel Electrophoresis

The genotype of each sample was visualised using gel electrophoresis with 10 ul of PCR product and 6× loading dye (Promega). The gel consisted of 80 ml of 1.5% DNA grade agarose (Progen) in 1×TBE and 2 ul of ethidium bromide (MP Biomedicals). Samples were run at 100 volts for 30 min alongside a 1 kb DNA ladder (Promega). It was expected that homozygous H5Rf/H5Rf mice DNA would have a single 237 bp band, heterozygous H5Rf/+ mice would have 237 bp and 565 bp bands and wild-type mice would have a single 565 bp band. Analysis of the gel showed that mice #10, 24 and 25 were homozygous (H5Rf/H5Rf) (data not shown). In some samples, an irrelevant transcript 1139 bp in length was observed (amplified with primers F3C and R2a).

Figure 4:
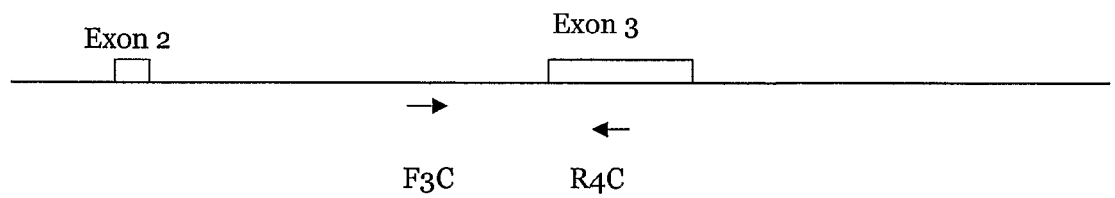
FIG. 4: Location of oligonucleotide primers used in PCR genotyping assay.
Figure 4:
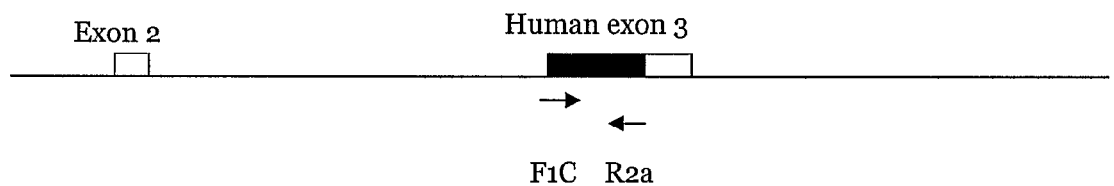

The relative location in the mouse/human C5aR locus of the PCR primers F1C, R2a, F3C and R4C used in the genotyping assay is shown in FIG. 4.

Example 5

Human C5aR is Expressed on Cells Isolated from Knock-in Mouse

To confirm that human C5a receptor is expressed in mice carrying the human C5aR gene neutrophils were isolated from the blood of a wild-type (+/+), a heterozygote (H5Rf/+) and a homozygote (H5Rf/H5Rf).

Direct Immunofluorescence Staining of C5aR in Whole Mouse Blood

Approximately 30 ul peripheral venous blood was collected from homozygous (H5Rf/H5Rf), heterozygous (H5Rf/+) and wild-type (+/+) mice in a tube containing EDTA (final concentration of EDTA was 5 mM). For detection of human C5aR receptor 30 ul blood was stained with 5 ul FITC (fluorescein isothiocyanate, Sigma)-labeled 7F3, an antibody specific for human C5aR (7F3 does not cross-react with mouse C5aR). Blood and antibody were incubated in a 12×75 mm test tube for 15 min at room temperature. To lyse erythrocytes and fix cells 500 ul BD Lysing Solution (Becton Dickinson) was added to the blood/antibody solution. After 15 min the cells were centrifuged at 1,200 rpm for 3 min at room temperature and the cell pellet was resuspended in 1 ml wash buffer (1×PBS, 0.1% BSA, 0.02% sodium azide). Cells were analysed in a FACS Calibur flow cytometer (Becton Dickinson) using Cell Quest software (Becton Dickinson). For each sample approximately 5,000 cells were counted.

Figure 5:
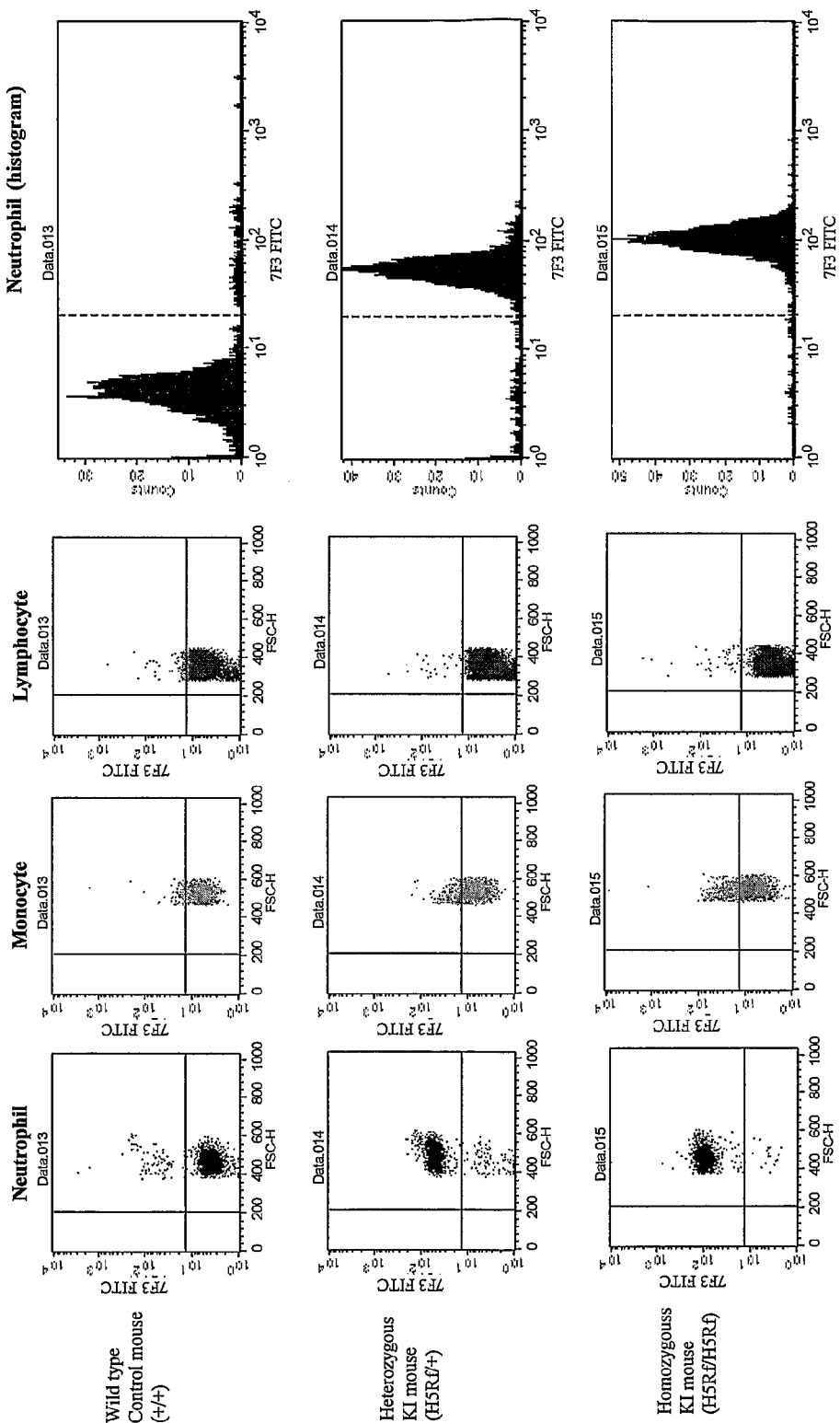
FIG. 5: FACS analysis showing human C5aR is expressed on neutophils in mice carrying the hC5aR gene. Blood from wild-type (+/+), heterozygous (H5Rf/+) and homozygous (H5Rf/H5Rf) mice was incubated with a human C5aR-specific antibody 7F3 conjugated to FITC. Area to the right of the broken line in the Neutrophil histogram is positive staining for 7F3-FITC.

FIG. 5 shows the results of this analysis. The neutrophils from both the homozygous and heterozygous KI mice bound 7F3, an antibody specific for human C5aR. In contrast, neutrophils from wild-type mice were not stained by 7F3. Lymphocytes from all genotypes of the mice were not stained with mAb 7F3. This was expected since C5aR is not expressed on lymphocytes. Monocytes from the homozygous and heterozygous knock-in mice were partially stained with 7F3, indicating a small percentage of the cells expressed human C5aR. No monocytes from the wild-type mouse were positive for 7F3 staining.

In summary, mice carrying the human C5aR gene express human C5aR on the surface of the cell types expected. This indicates that the mouse cell is able to express and process the human C5a receptor.

Example 6

Human C5aR Knock-in Mice can be Used to Screen Anti-Inflammatory Compounds

To demonstrate the utility of the human C5aR knock-in mice we subjected homozygous (H5Rf/H5Rf) mice to a model of inflammatory disease, namely, the K/BxN model of rheumatoid arthritis.

K/BxN TCR transgenic (tg) mice express a transgene-encoded (T cell receptor) TCR reactive to a self-peptide derived from the ubiquitously expressed glycolytic enzyme, glucose-6-phosphate isomerase (GPI), presented by the MHC class II molecule Ag7. These animals spontaneously develop a very aggressive form of arthritis, beginning at 3 to 4 wk of age. As in humans, the disease is chronic, progressive, and symmetrical, and it exhibits most (although not all) of the clinical, histological, and immunological features of RA in humans. Histological features include leukocyte invasion, synovitis, pannus formation, cartilage, and bone destruction. The murine disorder, critically dependent on both T and B cells, is joint specific but is initiated, then perpetuated, by T, then B, cell autoreactivity to a ubiquitously expressed antigen, GPI.

Strikingly, transfer of serum (or affinity purified anti-GPI IgGs) from arthritic K/BxN mice into healthy animals provokes arthritis within days, even when the recipients are devoid of lymphocytes.

Serum Transfer Protocol, Antibody Treatment and Arthritis Scoring.

Sera from arthritic K/BxN mice at 60 d of age were pooled and injected intraperitoneally (i.p.) (150 ul total volume) into 6-9 week old homozygous (H5Rf/H5Rf) and wild-type (+/+) mice on each of days 0 and +2. Sterile antibody (200 ug mouse anti-human C5aR antibody 7F3—isotype IgG2a or 200 ug isotype IgG2a control antibody) in PBS was injected i.p. into mice on each of days −1 and +3.

Arthritis was scored by clinical examination daily over 10-14 days. The severity of arthritis in each affected paw was graded as follows:

0 point: no evidence of inflammation
  1 point: subtle inflammation (metatarsal phalanges joints, individual phalanx or localised oedema)
  2 points: easily identified swelling but localised to either dorsal or ventral surface of paw
  3 points: swelling on all aspects of paw The sum of the scores from all four paws in each mouse was defined as the clinical score (maximum score per animal=12) and represents overall disease severity and progression in an animal.

Ankle thickness was measured using a calliper everyday. The thickness of each hind ankle was measured twice and an average of the 4 measurements calculated. Ankle thickening was defined as the difference in ankle thickness from the day 0 measurement. Mice were weighed daily.

Histology

The basic procedure of fixation, decalcification, paraffin sections, and hematoxylin/eosin staining of joint sections are as described (Kouskoff et al., 1996, supra). For immunohistology, unfixed and undecalcified cryostat sections are obtained. In brief, dissected ankle joints without skin are embedded in OCT, frozen in dry ice isopentane, and mounted on a cryomicrotome support at −25° C. After trimming the tissue block to a desired level, transparent tape is fastened onto the section surface of the block. Sagittal sections (6 or 8 mm thick) are cut underneath the tape, and the tissue is subsequently transferred to an adhesive-coated slide. Slides are stored at −80° C. until use, then acetone-fixed for 30 s to 1 min and air dried for 30 min. Nuclei are counterstained with 50 ng DAPI (Molecular Probes).

Homozygous Human C5aR Knock-in Mice Develop Inflammatory Disease.

To induce inflammatory disease the homozygous human C5aR knock-in mice (on C57BL/6 background) and wild-type/control (C57BL/6) mice were injected with K/BxN serum. Previous studies have determined the optimum dose of serum required and the expected time course of inflammation in the K/BxN model of rheumatoid arthritis. In this experiment all mice were injected i.p. with 2 lots of 150 ul of serum collected from arthritic K/BxN mice. It was expected that the wild-type mice would show signs of inflammation within 4 days of serum injection.

We would also expect the human C5aR knock-in mice to show signs of inflammation if the hC5aR gene is expressed and the receptor protein is processed correctly and is coupled to the G-protein signalling system. Firstly, the affinity of human C5a for the C5a receptor in mouse and human cells is very similar (Woodruff et al, 2001, Inflammation, v25, p 171-177) suggesting that the affinity of mouse C5aR for the human C5a receptor would be similar to its affinity to mouse C5aR. Secondly, studies with C5aR deficient mice have shown that the absence of C5aR prevents inflammation in the K/BxN model (Ji et al, 2002, Immunity, v16, p 157-168). Therefore, if the human C5aR gene was not expressed, or the human C5aR receptor was not functioning correctly then the homozygous hC5aR mice would not show signs of inflammation after K/BxN serum injection.

Figure 6:
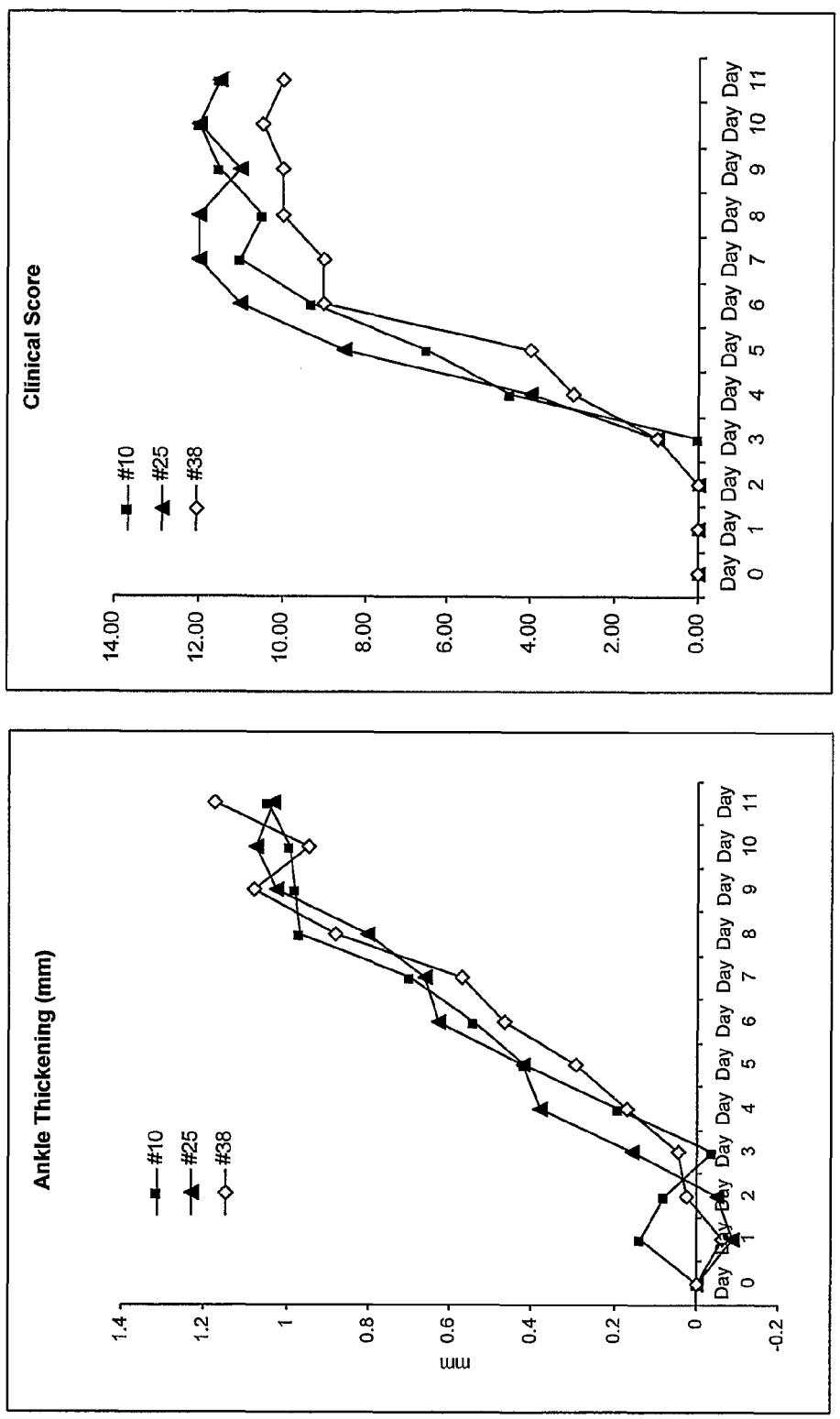
FIG. 6: Progression of RA-like inflammatory disease in homozygous human C5aR knock-in and wild-type mice. The left panel shows the increase in ankle thickness after K/BxN serum was injected i.p. on days 0 and 2. The right panel shows the clinical score. Mice #10 and #25 are homozygous for the human C5aR gene, mouse #38 is a wild-type littermate. Ankle thickening and clinical disease developed in both wild-type and homozygous hC5aR gene mice in the typical fashion described for this model (Lee et al (2002) Science, 297, 1689-1692).

In this model the outward clinical signs of inflammation are oedema and reddening of the paws, particularly the hind paws. Before and every day after serum injection mice were weighed and their hind ankle thickness measured, and a clinical score determined as described above. FIG. 6 shows the increase in ankle thickness and clinical score for wild-type and homozygous mice injected with the K/BxN serum. The progression of disease in the homozygous hC5aR knock-in mice was the same as in the control mice with inflammation apparent starting on day 3 after serum injection. This demonstrates that the expression and processing of the human C5a receptor in the knock-in mice is normal.

Histological examination of the cross section of ankle taken from mice on day 13 after serum injection in this model reveals bone erosion and infiltration of leukocytes into the synovial joint. The extent of tissue destruction, and accumulation of leukocytes was similar in the homozygous hC5aR knock-in mice and the control mice (data not shown).

Homozygous Human C5aR Knock-in Mice can be Used to Test Compounds for Anti-Inflammatory Properties.

The human C5aR knock-in mice were developed as a useful tool to screen anti-human C5aR compounds for anti-inflammatory activity. To test the utility of the mice we administered both homozygous hC5aR and wild-type (control) mice an antibody specific for human C5aR (it does not bind to mouse C5aR) or a control antibody (same isotype but irrelevant specificity) in the K/BxN model and determined the effect of the antibody on inflammatory disease progression. The antibody was injected i.p. twice (200 ug per dose), one day before and one day following the first K/BxN serum injection. Mice were monitored as described above.

Figure 7:
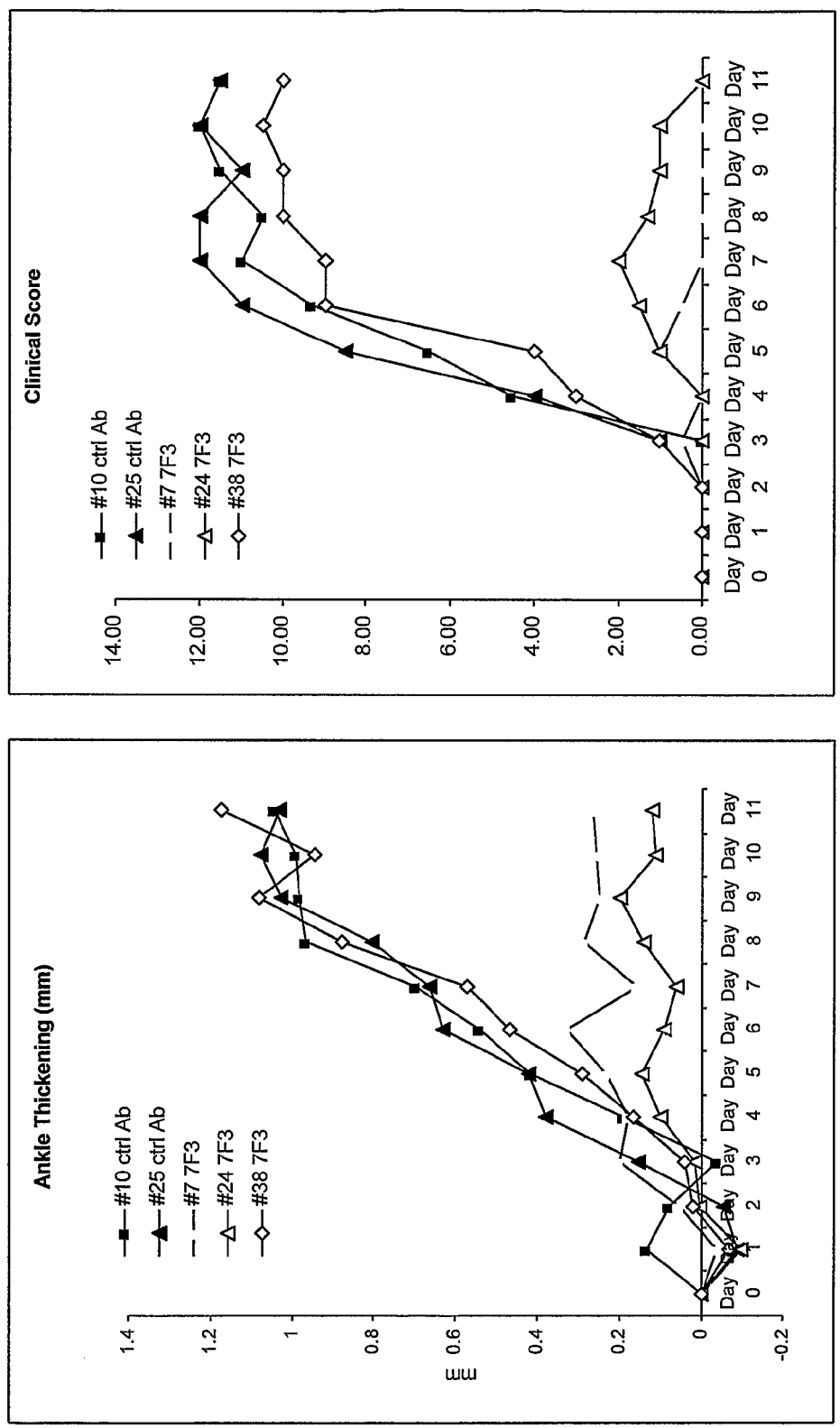
FIG. 7: Graphs showing progression and prevention of RA-like inflammatory disease in homozygous human C5aR knock-in mice. The left panel shows the increase in ankle thickness after K/BxN serum was injected i.p. on days 0 and 2. The right panel shows the clinical score. Mice #7, 10, 24 and 25 are homozygous for the humanC5aR gene. Mice #7 and #24 were injected with the human C5aR neutralising antibody 7F3, whereas mice #10 and #25 were injected with isotype control antibody. Wild-type littermate (mouse #38) was also treated with 7F3. Antibody was injected on days −1 and +3. The mice injected with control antibody developed an inflammatory disease. In contrast the hC5aR knock-in mice injected with 7F3 were protected from inflammation. Wild-type mice injected with 7F3 were not protected from inflammation.

FIG. 7 shows the clinical disease progression and ankle thickening in mice over the course of the experiment. The homozygous hC5aR knock-in mice injected with control antibody developed swelling and other signs of inflammation. In contrast the hC5aR knock-in mice injected with the anti-human C5aR antibody 7F3 did not develop clinical signs of inflammation. Control (wild-type) mice treated with 7F3 developed inflammation as evidenced by the increase in ankle thickness—as expected since 7F3 specifically binds human C5aR and does not bind mouse C5aR.

Furthermore, histological analysis revealed that mice injected with the anti-human C5aR antibody did not have tissue damage—the architecture of the synovial joint appeared normal with no signs of bone erosion, or excessive leukocyte infiltration—when compared to the ankles of mice injected with control antibody (data not shown).

This data clearly shows that the human C5aR knock-in mice are useful for testing compounds for anti-inflammatory activity in inflammatory disease models.

All publications referred to above are incorporated herein in their entirety by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A transgenic mouse comprising a polynucleotide encoding a human C5aR or humanized C5aR, wherein the C5a endogenous to the mouse binds to and effects signalling of the human or humanized C5aR, wherein said signalling is capable of inducing arthritis upon administration of sera from arthritic K/BxN mice, and wherein the transgenic mouse is homozygous for the polynucleotide encoding a human or humanized C5aR and wherein the endogenous C5aR coding sequences are disrupted.

2. The transgenic mouse according to claim 1, wherein the polynucleotide encodes human C5aR comprising the amino acid sequence as shown in SEQ ID NO:3, or an allelic variant thereof.

3. The transgenic mouse according to claim 1, wherein the polynucleotide comprises the nucleotide sequence as shown in SEQ ID NO:2, or an allelic variant thereof.

4. The transgenic mouse according to claim 1, wherein the polynucleotide encodes humanized C5aR.

5. The transgenic mouse according to claim 4, wherein the humanized C5aR comprises a C5aR sequence endogenous to the mouse wherein at least one extracellular or intracellular domain is replaced with the corresponding human C5aR domain.

6. The transgenic mouse according to claim 1, wherein the endogenous C5aR coding sequences have been replaced with a corresponding human C5aR coding sequence.

7. An isolated cell(s), cell line, tissue or organ obtained from the transgenic mouse of claim 1, the isolated cell, cell line, tissue or organ comprising a polynucleotide encoding a human C5aR or humanized C5aR.

8. A method for producing a transgenic mouse for testing compounds for an effect on a phenotype associated with C5aR signalling, the method comprising:
    introducing into the genome of a mouse a polynucleotide construct encoding human C5aR, humanized C5aR or a fragment of human C5aR to produce a transgenic mouse, wherein the C5a endogenous to the mouse binds to and effects signalling of the human or humanized C5aR, wherein said signalling is capable of inducing arthritis upon administration of sera from arthritic K/BxN mice, and wherein the endogenous C5aR coding sequences are disrupted.

9. The method according to claim 8, wherein the polynucleotide construct encodes human C5aR.

10. The method according to claim 9, wherein the polynucleotide construct encodes a polypeptide comprising the amino acid sequence as shown in SEQ ID NO:3, or an allelic variant thereof.

11. The method according to claim 9, wherein the polynucleotide construct comprises the nucleotide sequence as shown in SEQ ID NO:2, or an allelic variant thereof.

12. The method according to claim 8, wherein the polynucleotide construct encodes humanized C5aR.

13. The method according to claim 8, wherein the polynucleotide construct encodes a fragment of human C5aR.

14. The method according to claim 13, wherein the fragment encompasses at least one extracellular domain of human C5aR.

15. The method according to claim 8, wherein the method comprises replacing the endogenous C5aR coding sequences, with a corresponding human C5aR coding sequence or fragment thereof.

16. A method for screening a candidate compound for anti-inflammatory activity in the transgenic mouse according to claim 1, or isolated tissue or cells obtained therefrom, the method comprising:
   administering a candidate compound to the transgenic mouse, wherein an inflammatory response is induced in the transgenic mouse by administration of sera from arthritic K/BxN mice; and
   examining an of the candidate compound on the inflammatory response in the transgenic mouse or isolated tissue or cells obtained therefrom;
   wherein a decrease in the inflammatory response in the transgenic mouse, or isolated tissue or cells obtained therefrom, as compared to the inflammatory response in the absence of the candidate compound, indicates the candidate compound has anti-inflammatory activity.

17. The method according to claim 16 wherein the candidate compound is selected from the group consisting of: a peptide, including a peptide derived from C5aR or C5a or other non-C5aR peptide and capable of inhibiting, reducing or repressing a C5aR function, a C5aR dominant-negative mutant; a non peptide inhibitor of C5aR; an antibody or antibody fragment which binds to C5aR and inhibits a C5aR function; a small organic molecule, a nucleic acid encoding said peptide derived from C5aR or C5a or other non-C5aR peptide inhibitor, an antisense nucleic acid directed against C5aR-encoding mRNA, an anti-C5aR ribozyme, and a small interfering RNA (RNAi) that targets C5aR gene expression.

* * * * *

UNITED STATES PATENT AND TRADEMARK OFFICE
CERTIFICATE OF CORRECTION

| | | |
|---|---|---|
| PATENT NO. | : 8,071,839 B2 | Page 1 of 1 |
| APPLICATION NO. | : 10/584480 | |
| DATED | : December 6, 2011 | |
| INVENTOR(S) | : Charles Reay Mackay | |

It is certified that error appears in the above-identified patent and that said Letters Patent is hereby corrected as shown below:

In claim 16, column 66, line 1, please replace "examining an of" with --examining an effect of--.

Signed and Sealed this
Third Day of April, 2012

David J. Kappos
*Director of the United States Patent and Trademark Office*